United States Patent [19]

Soma et al.

[11] Patent Number: 5,281,583
[45] Date of Patent: Jan. 25, 1994

[54] LPS-CONTAINING ANALGESICS AND VETERINARY ANALGESICS

[75] Inventors: Gen-Ichiro Soma, 1-10-21, Higashi-Tamagawa, Setagaya Ward, Tokyo; Kiyoshi Yoshimura; Daisuke Tsukioka, both of Chiba; Den'Ichi Mizuno, Okamoto-18, Kamakura City, Kanagawa; Haruyuki Oshima, Hachioji, all of Japan

[73] Assignees: Den'Ichi Mizuno, Kanagawa; Gen-Ichiro Soma, Tokyo, both of Japan

[21] Appl. No.: 748,808

[22] Filed: Aug. 22, 1991

Related U.S. Application Data

[63] Continuation-in-part of Ser. No. 747,728, Aug. 20, 1991, abandoned.

[30] Foreign Application Priority Data

Aug. 20, 1990 [JP] Japan .................. 2-218599
Nov. 20, 1990 [JP] Japan .................. 2-312932

[51] Int. Cl.⁵ .................. A61K 31/70; A61K 31/715
[52] U.S. Cl. .................. 514/23; 514/54
[58] Field of Search .................. 514/23, 54

[56] References Cited

U.S. PATENT DOCUMENTS

| | | | |
|---|---|---|---|
| 4,454,119 | 6/1984 | Fukushi | 424/170 |
| 4,528,188 | 7/1985 | Mitsuhashi et al. | 536/1.1 |
| 4,612,304 | 9/1986 | Fukushi | 514/53 |
| 4,929,604 | 5/1990 | Munford et al. | 514/53 |

OTHER PUBLICATIONS

Seppala, et al., Chem. Abst. 102:44031q, 1985.
Jacobs, et al., Chem. Abst. 85:141214q, 1976.

*Primary Examiner*—John W. Rollins
*Attorney, Agent, or Firm*—Kazuyuki Yamasaki

[57] ABSTRACT

An analgesic composition comprising an effective amount of at least one member of LPS whose macrophage activation $ED_{50}$ is 0.4–100 ng/ml of culture solution in terms of its limulus test-positive LPS content observed on a sigmoid curve prepared by determining the ability of the LPS to activate the TNF productivity of macrophage cultured in vitro, and plotting the macrophage activation ability (%) along the axis of ordinate wherein the ability is estimated to be 0% in the case where it corresponds to the quantity of TNF produced by macrophage with no LPS added thereto, and 100% is assigned to the macrophage activation ability which provides the maximal and constant quantity of TNF produced by the macrophage and plotting the limulus test-positive LPS content of the LPS along the axis of abscissa on a logarithmic scale, in admixture with a pharmaceutically or veterinarily acceptable carrier, such that when administered to an animal, high cholesterol level of said animal is prevented or cured; and a method of treating pain of an animal comprising administration to said animal an amount of the above composition effective to prevent or cure the pain of said animal.

2 Claims, 6 Drawing Sheets

LPS-CONTAINING ANALGESICS AND VETERINARY ANALGESICS

This application is a continuation-in-part of U.S. application Ser. No. 07/747,728, filed Aug. 20, 1991, now abandoned.

FIELD OF THE INVENTION

The present invention relates to novel analgesics, and novel veterinary analgesics.

More particularly, it is concerned with novel analgesics and novel veterinary analgesics containing LPS.

DESCRIPTION OF THE PRIOR ART

Analgesics are classified into two groups; narcotic and non-narcotic ones.

Narcotic analgesics are of course narcotics, and thus they are required to be administered with the greatest care. ("Clinical pains", pp. 70-74, 1981, *Medical Friend Co.* in Japan)

On the other hand, generally the analgesic action of non-narcotic analgesics is characterized to be less than that of narcotic ones and to be nonhabit-forming. But, actually their prolonged use is reported to cause tolerance and/or dependence of the patients thereto, and thus they are considered to be used in the same manner as narcotic-ones from pharmacological viewpoints. ("Clinical pains", p. 74, supra)

Thus the prior art analgesics have drawbacks, and no satisfactory ones have not been provided yet. Particularly, analgesics which are effective against chronic pain, are highly safe, have no side effects, are cheap and are very convenient for medication have been greatly expected to be developed.

BRIEF SUMMARY OF THE INVENTION

The present invention is intended to provide novel analgesic agents, and veterinary analgesic agents which are free from the drawbacks of the prior art.

An additional object of the present invention is to provide novel analgesics and veterinary analgesics which show a high therapeutic range, and may be provided at a low cost and in a large amount and may be administered via any route of oral and intradermal administration and injection.

DETAILED DESCRIPTION OF THE INVENTION

Figure 1:
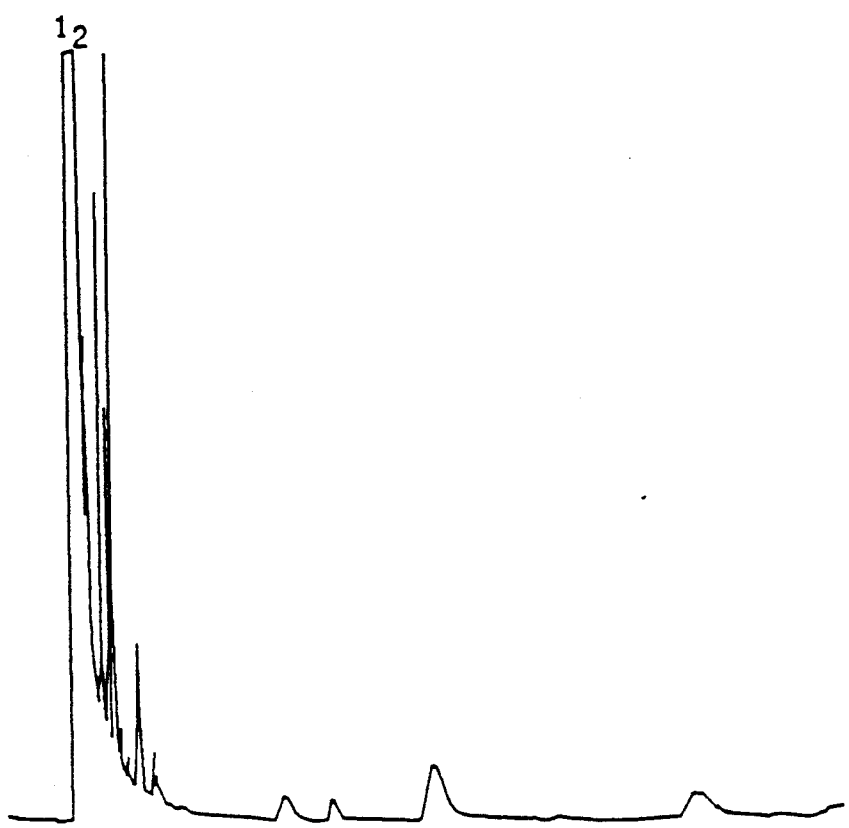
FIG. 1 is a gas chromatographic chart of wheat LPS, showing the peaks evidencing the presence of fatty acids therein.

The LPS available for use as an active ingredient of analgesic and veterinary analgesic agents according to the present invention may be chosen regardless of its source, process for its production and purification or the like. For example, the LPS may be any one extracted from bacteria or plants, or may be a synthetic one such as synthetic lipid A. Here, throughout the specification and particularly in the claims, the LPS qualified with its source should not be interpreted to be restricted only those obtained from the specified source. Instead, it should be interpreted that the LPS include, in addition to those from the specified source, all the LPS obtained from bacteria or the like which grow on, in or together with the specified source during the course of its growth, storage, distribution or the like. For example, wheat LPS should be interpreted to include not only LPS from wheat, but also all the LPS obtained from bacteria or the like which grow on, in or together with wheat during the course of its growth, storage, distribution or the like. This is because it is well known in the art that, besides the hitherto known parasitic plants and animals, many types of organisms are allowed to grow on, in or together with certain plants, animals, or organisms belonging to mycota or lichenes.

Of the above-mentioned LPS, the LPS available for use as an active ingredient of aanlgesics or veterinary analgesics according to the present invention include those whose macrophage activation $ED_{50}$ is 0.4-100 ng/ml of culture solution in terms of its limulus test-positive LPS content observed on a sigmoid curve prepared by determining the ability of the LPS to activate the TNF productivity of macrophage cultured in vitro, and plotting the macrophage activation ability (%) along the axis of ordinate wherein the ability is estimated to be 0% in the case where it corresponds to the quantity of TNF produced by macrophage with no LPS added thereto, and 100% is assigned to the macrophage activation ability which provides the maximal and constant quantity of TNF produced by the macrophage, and plotting the limuius test-positive LPS content of the LPS along the axis of abscissa on a logarithmic scale.

"Macrophage" is the generic name for large amoeba-like cells which belong to immunocompetent cells, are present in most internal tissues of animals, and prey and digest particulate foreign matter and waste cells in the body.

"TNF" is the generic name for tumor necrosis factors produced by macrophage (*The Journal of Biol. Chem.*, 260, pp. 2345-2354, 1985), and the production quantity of TNF increases depending on the activity of macrophage.

"Limulus test" is a method invented by Levin in 1968 for quantitative determination of endotoxin using a horseshoe crab haemocyte extract and a chromogenic substrate.

Limulus test-positive vegetable LPS

The plants available for use as the starting material to prepare the cholesterol-lowering agents and veterinary cholesterol-lowering agents according to the present invention will be exemplified below.

For example, any plant belonging to Gymnospermae, Monocotyledoneae, Dicotyledoneae, Pteridophyta, Algae or Fungi may be used separately or in admixture with each other.

The plants belonging to Gymnospermae available for use in the present invention include, for example, pine (Pinus spp.) belonging to Pinaceae.

Illustrative embodiments of the plants belonging to Monocotyledoeae available for use in the present invention are rice (*Oryza sativa* L.), wheat (*Triticum sativum Lamarck, Triticum aestivum* L.), barley, rye, oats (*Avena fatua.*), *Sasa albomarginata*, and pearl barley (*Coix Lacryma-jobi L. var. Ma-yuen Stapf*) belonging to Gramineae; blue flag (*Iris sanguinea Donn., Iris Nertschinskia Lodd.*) belonging to Iridaceae; garlic (*Allium sativum* L.), asparagus (*Asparagus officinalis* L.) and dwarf lilyturf (*Ophiopogon japonicus Ker-Gawl. var. genuinus Maxim., O. japonicus Ker-Gawl.*) belonging to Liliaceae; ginger (*Zingiber officinale Roscoe*), Japanese ginger (*Zingiber mioga*) and turmeric (*Carcuma domestica Valeton, Carcuma longa* L.) belonging to Zingiberaceae; jack-in-the-culprit (*Arisaema triphyllum*), etc.

The plants belonging to Dicotyledoneae available for use in the present invention are, for example, those belonging to Rubiaceae, Cruciferae, Cucurbitaceae, Lauraceae, Juglandaceae, Piperaceae, Umbelliferae, Menispermaceae, Saururaceae, Solanaceae, Rosaceae, Actinidiaceae, Leguminosae, Rutaceae, Magnoliaceae or Myristicaceae. More particularly, soybean (*Glycine Max Merill*), "adzuki" bean (*Azukia angularis Ohwi*), broad bean (Vicia L.), kudzu (*Pueraria thunbergiana*), and licorice (*Glycyrrhiza glabra L. var. glandulifera Regel et Herder*) belonging to Leguminosae: potato (*Solanum tuberosum* L.), tomato (*Solanum lycopersicum* L., *Lycopersicum esculentum Mill.*), and red pepper (*Capsicum annuum* L.) belonging to Solanaceae; loquat (*Eribotrya japonica Lindl.*) and peach (*Prunus persica Batsch., Prunus persica Batsch. var. vurgalis Maxim.*) belonging to Rosaceae; avocado (*Persea americana Mill.*) belonging to Lauraceae; walnut belonging to Juglandaceae; pumpkin (*Cucurbita moschata Duch.*) and *Gynostemma pentaphyllum* (Thunb.) belonging to Cucurbitaceae; kaiware daikon (Japanese radish) belonging to Cruciferae; silvervine (*Actinidia polygama Maxim.*) belonging to Actinidiaceae; *Houttuynia cardata* Thunb. belonging to Saururaceae; pepper (*Piper nigrum* L.) belonging to Peperaceae; *Illicium verum Hook. fil.*; nutmeg (*Myristica fragrans Houtt.*) belonging to Myristicaceae; sour orange (*Citrus aurantium L. subsp. amara Engi., Citrus bigaradia Risso et Pointean*) belonging to Rutaceae; "otane ninjin" (otane carrot) belonging to Araliaceae; *Seseli libanotis Koch var. daucifolia DC.* belonging to Umbelliferae; *Sinomenium acutum Rehd. et Wils.* belonging to Menispermaceae; *Uncaria rhychophylla Miq., Ourouparia rhynchophylla Matsum.* belonging to Rubiaceae, etc. may be used.

The plants belonging to Pteridophyta available for use according to the present invention are, for example, horse tail (*Equisetum arvense* L.) belonging to Equisetaceae; royal fern (*Osmunda japonica Thunb.*) belonging to Osmundaceae, etc.

As plants belonging to Algae, any one belonging to, for example, Phaeophyceae, Rhodophyceae, Chlorophyceae or Cyanophyceae may be used separately or in admixture with each other. Illustrative embodiments of those belonging to Phaeophyceae are *Undaria pinnatifida Suringar* and kelp (*Laminaria japonica*) belonging to Laminariaceae; *Hizikia fusiformis* belonging to Sargassaceaeu, etc. Illustrative embodiments of those belonging to Rhodophyceae are asakusa laver (*Porphyra tenera*) belonging to Bangiaceae, etc. Illustrative embodiments of those belonging to Chlorophyceae are chlorella (Chlorella) belonging to Oocystaceae, etc.

As a fungus available for use according to the present invention, for example, any one belonging to Basidiomycetes or Ascomycetes may be used separately or in admixture with each other. Illustrative embodiments of those belonging to Basidiomycetes are *Lentinus edodes Sing., Cortinellus shiitake P. Henn.*; winter mushroom (*Flammulina velutipes*); *Lyophyllum shimeji;* maitake (phonetically spelled); awabitake (phonetically spelled) belonging to Polyporaceae; mushroom (*Agaricus bisporus, Agaricus bitorquis*); Jew's ear (*Hirneola auricula-judae Berk., Auricularia auricula-judae Quel*) belonging to Auriculariaceae; *Pholiota nameko*. Illustrative embodiments of those belonging to Ascomycetes are baker's yeast and brewer's yeast belonging to Saccharomycetaceae. Here the "brewer's yeast" include those for brewing beer, sake (a Japanese alcohoric beverage) or wine or making shoyu (a Japanese soy sauce) or miso (a Japanese food paste made of soybeans, etc.), and further many other types of yeast belonging to Saccharomycetaceae and used for the preparation of whiskey, samshu (a Chinese alcohoric beverage) or the like. Also *Cordyceps sinensis Sacc., Cordyceps, sobolifera* belonging to Clavicipitaceae may be used according the present invention.

Detection and quantitative determination of limulus test-positive LPS

The detection of the limulus test-positive LPS contained in any one of the plants referred to above and the determination of their LPS content may be carried out by using, for example, a reagent set commercially available from Sei-Kagaku Kogyo Co. in Japan under the trade name of Toxi Color System. That is, the starting plant is contacted with LS-1 set of said system, and the chromogenic strength of the plant is determined in comparison with the data of the calibration curve prepared using the ET-2 set of said system.

The vegetable LPS may be separated and purified in such a manner as mentioned below.

Separation and purification of limulus test-positive vegetable LPS

1) The starting plant is, if necessary after being sliced, dried and pulverized appropriately, suspended in distilled water, and then the supernatant is collected.

For example, in case the starting plant is supplied in the form of cereal seeds, then the seeds are, if necessary or desired, after the removal of the seed coats, somewhat crushed or pulverized to an edible particle size of powders. The resulting powders are prepared as a dispersion by addition of water thereto, and stirred. The dispersion is allowed to stand or subjected to centrifugation to remove the sediment, or the dispersion is worked into a dough by kneading, and is gently washed with water in a mixer to remove the sediment.

In the case where chlorella is used as the starting plant, then it is recommended first to crush the cell membranes, and then to wash the cells with ethanol to remove off the fatsoluble matter prior to the extraction with water.

When the above extraction is effected, there is no need to put limitations on the particle size of the starting plant, the temperature, the properties and the quantity of the water, the speed and the time of the stirring and the centrifugation conditions. These conditions may be adjusted conventionally depending on the starting plant used. Surely the water for extraction at a higher temperature tends to provide a larger quantity of a higher purity. For convenience only, however, the temperature of the water for the extraction is desired to be not more than 50° C. so that the starch in the starting plant is not gelatinized. In addition, though the quantity of the water to be added changes depending on the type and the particle size of the staring plant used, for easiness of operation only, it is desired to be 20-50 w/v %. At the end of this stage of operation, the purity of the limulus test-positive vegetable LPS plant of the present invention increases to about 30-fold value in the case of wheat seeds judging from the data on limulus test activity.

Hereunder, the description of the specification will made with particular reference to the case where cereal seeds are used as the starting material. But, no doubt it is sure that the teachings found in such description are sufficient for any person skilled in the art to remove off sugars, proteins and other useless components from another starting material thereby extracting the limulus test-positive LPS of a high purity available for use according to the present invention.

2) In order to get a higher purity, the supernatant from the above 1) may be subjected to ultrafiltration in the conventional manner to remove fractions having molecular weights of 5,000 or less.

3) The resulting dried sample is then suspended in distilled water to a proportion of 50 mg/ml after which it is subjected to centrifugation to collect the supernatant.

4) The supernatant from the above 3) is cooled on ice water, and then an acid added thereto to produce sediment. Here, any acid may be employed; for example, trichloroacetic acid (hereunder referred to as TCA only), perchloric acid, trifluoroacetic acid, acetic acid or dichloroacetic acid may be employed.

5) Then the mixture is subjected to centrifugation to collect the sediment which is then washed with distilled water, and then is subjected to centrifugation again to collect the sediment.

6) The sediment from the above 5) is suspended in distilled water, and an alkali is added to the suspension until the sediment dissolves therein. Here, any alkali may be used; for example; sodium hydroxide, potassium hydroxide, ammonia, sodium carbonate, sodium acetate or the like may be used. Here, care should be taken that the basicity of the suspension does not go over pH 11 when the sediment dissolves in order to keep the object LPS from being deactivated.

7) Then an acid is added to the suspension to bring its pH to pH 8 followed by warming to 37° C. Further addition of an acid makes the suspension basic to produce sediment which is then collected by a centrifuge warmed at 37° C.

8) The thus collected supernatant is cooled on ice, and then subjected to centrifugation at 4° C. again.

9) The supernatant is collected, and then neutralized by the addition of an alkali, and concentrated by ultrafiltration in the conventional manner. Here, any alkali may be used.

10) Then the concentrate is subjected to gel filtration in the conventional manner, and limulus test-positive fractions are collected and combined. Here, the support for the gel filtration may be, for example, Sephadex G-75, G-100, Sephacryl S-200, Sepharose 6B (the foregoing are all manufactured by Pharmacia Inc. in U.S.), Biogel P-100 (manufactured by Biorad Inc.), Toyo Pearl HW-50, HW-55 (manufactured by Toyo Soda Kogyo Co. in Japan), or the like. The buffer solution may be any one as long as it can keep the pH within the range of 3-10. For example, Tris-HCl or phosphate buffer solutions may be used.

11) Then a proteolytic enzyme is added to the combined fractions which are then incubated at 37° C. for 2 or more hours to decompose the remaining proteins. The thus treated solution is then concentrated by ultrafiltration in the conventional manner. Here, no specific proteolytic enzyme is required, and, for example, V8 protease, chymotrypsin, trypsin or thermolysin may be used separately or in optional combinations thereof. The commercially available proteolytic enzymes which may be used according to the present invention include, for example, Pronase ® (Kaken Kagaku Co. in Japan) and Proteinase ® (Merc Co. in U.S.)

12) Then the collected fractions are treated conventionally, for example, by being subjected to ion-exchange chromatography using mono Q Sepharose or Q Sepharose manufactured by Pharmacia Inc., to collect the limulus test-positive fractions.

13) Then, the fractions are subjected to gel filtration conventionally to collect the desalted limulus test-positive fractions.

By the above-mentioned procedures, in the case of wheat seeds, about 20% of the originally present limulus test-positive matter is recovered, and a purified sample of about 95% purity is obtained. This value achieved in the case of wheat seeds is about 1,000 times as high as that obtained at the end of 1) referred to above.

The limulus test-positive vegetable LPS prepared according to the above procedures and other LPS within the purview of the present invention may be supplied as such, or in the forms diluted to an optional desired degree. In addition, in order to improve its stability, they may be supplied as dried powders in the conventional manner including lyophilization and spray drying. Each of these forms may be produced conventionally.

Limulus test-positive bacterial LPS

The hitherto known *E. coli* LPS, LPS provided by A. radiobacter (P. H. Graham and M. A. O'Brien, "*Antonic van Leeuwenhock*", vol. 34, pp. 326-330, 1968, hereunder will be referred to only as A. radiobacter LPS, B. pertussis LPS, lipid A, etc., and LPS1, LPS2 and LPS3 mentioned later and mixtures of them satisfy the requirements. the.

*E. coli* LPS is commercially available from, for example, Difco Co. in U.S.A.

*B. pertussis* LPS is commercially available from, for example, Funakoshi Yakuhin (Funakoshi Pharmaceuticals Co.) in Japan. Alternatively, B. pertussis LPS may be prepared from dead cells of any publicly known B. pertussis, for example, Tohama I phase strain, by any of the publicly known processes described, for example, in the following literature:

Webster, et al., "*J. Immunol.*", 744, 55, 1955; and
Westphal, et al., "*Z. Naturforsch*", 76, 148, 1952.

Lipid A is commercially available from, for example, Dai-ichi Kagakuyakuhin (Dai-ichi Chemicals Co.) in Japan.

The three bacteria according to the present invention were isolated from all kinds of wheat investigated by the inventors of the present invention regardless of their places of production. Thus, those bacteria are supposed to be isolated from any kind of wheat produced in any place and its processed goods. The kinds and the places of production of the wheat flour from which the three bacteria mentioned above were confirmed to be isolated by the inventors of the present invention include the following:

| Kinds of wheat flour | Places of production |
| --- | --- |
| Dark Northern Springs | U.S.A. |
| 1 Canadian Wheat | Canada |
| Hard Red Winter Semi-hard | U.S.A. |
| Australian Standard Wheat | Australia |
| Horoshiri | Japan |

The LPSs of the present invention may be isolated from the above bacteria by the hot phenol process described on page 83 of Westphal, et al., "Methods in Carbohydrate Chemistry", vol. v, 1965, Academic press in New York, followed by purification on an anion-exchange resin.

That is, the cells are suspended in distilled water which is then stirred with an equivolume of hot phenol. Next, the aqueous layer is recovered by centrifugation and then subjected to dialysis to remove off the phenol. The aqueous layer is concentrated by ultrafiltration to yield crude LPS fractions which are then purified conventionally, for example, by anion-exchange chromatography using mono Q-Sepharose and Q-Sepharose in FPLC system (all manufactured by Pharmacia Inc.), followed by desalting in a conventional manner.

Products of 96% or more purity are provided by the foregoing procedures.

Determination of ability of the LPS according to the present invention to activate in vitro TNF productivity of macrophage Carswell et al. report that priming and triggering steps are necessary to produce endogenous TNF in the body of an animal; see Proc. Natl. Acad. Sci. USA., 72, pp. 3666-3670, 1975. Thereafter, many candidate chemicals were tried to stimulate the respective steps. The chemical used to start the priming step is a primer (endogenous TNF production stimulator), while that administered to start the triggering step is a trigger (endogenous TNF productive agent).

In order to determine the ability of LPS to activate the in vitro TNF productivity of macrophage, a recombinant mouse IFN-$\gamma$ is added to peritoneal macrophage cells of mouse as the primer followed by addition of the LPS as the trigger thereto, and then the TNF activity is determined.

The TNF activity is determined, as follows, on the basis of the cytotoxicity to L929 cells (Proci. Natl. Acad. Sci. U.S.A., 72, pp. 3666-3670, 1983). L-929 cells are cultured in Eagles' Minimum Essential Medium (hereunder referred to only as MEM) with 5% fetal calf serum (hereunder referred to only as FCS) added thereto until 100 $\mu$l of the medium contains $8 \times 10^4$ cells, and then the cells are grown in a flat-bottomed plate having 96 wells.

The growth conditions are 37° C. in the presence of 5% $CO_2$, and under a humidity of 100% for 2 hours, and the procedures may be the same as for the conventional cell culture. Then actinomycin D is added to the medium to a final concentration of 1 $\mu$g/ml, and the volume of the culture solution is adjusted to 150 $\mu$l. Immediately thereafter 50 $\mu$l of the sample diluted appropriately with MEM medium is added to the culture solution. Here, $ED_{50}$ may be determined by adjusting the dilution appropriately. The L-929 cells having a final volume of 200 $\mu$l are cultured for an additional 18 hours under the same conditions as described above.

In order to determine the cell necrosis activity, first the whole medium is removed followed by addition of a 1% methyl alcoholic solution containing 0.1% crystal violet for fixation staining. Crystal violet stains all the eukaryotic cells, but the dead cells are removed off from the bottom of the flask only by washing after the staining; so the cell necrosis activity may be determined directly. The staining degree is measured on the basis of adsorption at $OD_{590 \; nm}$, and is compared with that of a control to determine the cell necrosis activity. This activity is defined as follows.

The dilution of the sample which allows 50% of the L-929 cells to survive (N) is determined. Rabbit TNS is used as the control, and its activity n (units/ml) is determined using $2.4 \times 10^6$ units/mg/ml of TNF-$\alpha$. The dilution which provides $ED_{50}$ of rabbit TNS is determined.

The activity of the sample (units/ml) is calculated by the equation $N/C \times n$.

Forms supplied

The analgesics and veterinary analgesics according to the present invention may be supplied conventionally in the form of powders, granules, pills, tablets, troches, capsules, solutions, pastes, ointments, liniments, lotions, suppositories, injections, etc. For veterinary use, also the agents may be prepared in the form of feed additives, premix preparations, drinking water additives. Here, the "premix preparations" are such preparations as contain feed components beforehand so that they are easily mixed in the feed. The feed additives are preferred to be powders or granules. Any commercially available feed may be used to prepare the above-mentioned feed additives, premix preparations, etc. The feed may contain minerals, vitamins, amino acids and any other feed additives.

If desired, these preparations may contain excipients, preservatives, buffers, etc. conventionally to improve the shelf life, homogeneity, etc. In addition, the preparations may contain correctives to improve taste, odor, appearance, etc. The excipients include, for example, lactose, starch, etc. The preservatives include, for example, parahydroxybenzoic esters such as methyl, ethyl or propyl paraoxybenzoate, sodium dehydroacetate, phenols, methyl, ethyl or propylparabene, etc. The buffers include, for example, citric, acetic or phosphoric acid salts, etc.

Determination of analgesic effects

The analgesic effects of the LPSs of the present invention have been confirmed by an experiment using animals according to the acetic acid-writhing method described on page 415 of "Inflammation and anti-inflammatory therapy" issued in 1982 by Ishiyaku Shuppan Co. in Japan, one of the established methods for the determination of the effects of non-narcotic analgesics. The experiment included comparison with the prior art phenylbutazone which is often used to eliminate inflammatory pain.

Hereunder, the present invention will be explained in detail with reference to examples, preparations and experiments. The E.coli LPS used therein is one available from Difco Co. in U.S.A. under the code number of 0128:B8. Sugar content was determined by the phenol-sulfuric acid process (M. Dubois et al., "Analytical Chemistry", vol. 28, p. 350, 1956), and protein content was determined by the Lowry process (O. H. Lowry et al., "Journal of Biological Chemistry", vol. 193, p. 65, 1951.)

REFERENCE EXAMPLE 1

(preparation of wheat LPS)

1) In a small kneader, there was charged 3,120 g of hard flour containing 1.09% of ash (Hard Red Spring wheat from U.S.A. or Canada) followed by addition of 2.03 l of distilled water thereto and kneading for 10 minutes to prepare a dough. The mixture was allowed to stand for 15 minutes, and then 10 l of water was added to the mixture followed by gentle stirring to extract a starch emulsion and to dissolve soluble ingredients in the water. The resulting solution was allowed to stand in a refrigerator at 5° C. for 12 hours, and then the sediment containing starch etc. was removed. The supernatant was lyophilized to get 201.1 g of powders (Powder A).

Then 5 l of distilled water was added to the residual dough followed by gentle stirring, and the mixture was treated in the same manner as the above to get 40.1 g of powders (Powder B).

2) The powders A and B were charged in an ultrafilter HF-Lab1 (Amicon Co.), and the ultrafiltration was carried out using a hollow cartridge HF-Lab1PM5 for fractions having a molecular weight of 5,000, and another hollow cartridge HF-Lab1PM10 for fractions having a molecular weight of 10,000; the temperature range was 5°–10° C., the inlet pressure was 25 p.s.i. (1.76 kg/cm$^2$), and the outlet pressure was 15 p.s.i. (1.06 kg/cm$^2$). As a result, the respective fractions were named as follows:

Powder A:
 Fractions having a molecular weight of 5,000 or less were named $a_1$.
 Fractions having a molecular weight of 5,000 or more were named $a_2$.

Powder B:
 Fractions having a molecular weight of 5,000 or less were named $b_1$.
 Fractions having a molecular weight of 5,000 or more were named $b_2$.

Powder A:
 Fractions having a molecular weight of 10,000 or less were named $a_3$.
 Fractions having a molecular weight of 10,000 or more were named $a_4$.

Powder B:
 Fractions having a molecular weight of 10,000 or less were named $b_3$.
 Fractions having a molecular weight of 10,000 or more were named $b_4$.

Each of these fractions was subjected to the limulus test according to the method detailed in Experiment 1 given later, and it was confirmed that much limulus test-positive ingredients are present in fractions having a molecular weight of 5,000 or more, whereas little limulus test-positive ingredients are present in fractions having a molecular weight of 5,000 or less.

3) Thirty grams of the above powder $a_2$ was placed in a 1 l Erlenmeyer flask after which 600 ml of distilled water was poured thereon. The resulting mixture was stirred with a stirrer for 60 minutes, and then subjected to centrifugation at 10,000 G for 10 minutes using a Hitachi cooling type high speed centrifuge SCR-20B (the rotor RPR16 was cooled to 4° C. beforehand) to recover the supernatant.

4) The supernatant from the above 3) was placed in another 1 l Erlenmeyer flask followed by dropwise addition of 20.5 ml of a 100% aqueous solution of TCA cooled to 2° C. beforehand while cooling on ice (the temperature of the solution was about 2° C.) and stirring with a stirrer. After the completion of the dropwise addition, the flask was allowed to stand in ice water for 10 minutes.

5) Next, the mixture was subjected to centrifugation (at 10,000 G for 10 minutes) at 4° C. in the same manner as the above to collect sediment which was in turn put in a 500 ml beaker together with 300 ml of distilled water while cooling in ice water to prepare a suspension. The resulting suspension was cooled in ice water and subjected to centrifugation (at 10,000 G for 10 minutes) at 4° C. in the same manner as the above to recover sediment.

6) The sediment was placed in a 1 l beaker followed by addition of 500 ml of distilled water to prepare a suspension. The resulting suspension was neutralized to pH 7 by the use of about 3.5 ml of 1N sodium hydroxide, and then, while cooling in ice water, about 2 ml of 1N sodium hydroxide was added to the neutralized suspension until a 0.02N sodium hydroxide solution is prepared to dissolve the sediment.

7) About 1.5 ml of 1N hydrochloric acid was added to the solution to bring the pH to 8 followed by addition of 100 ml of distilled water. The solution was transferred to a 1 l Erlenmeyer flask which was then shaken slowly in an incubator at 37° C. for 30 minutes.

8) The solution from the above 7) was mixed with 30 ml of a 100% aqueous solution of TCA, and then slowly shaken in an incubator at 37° C. for 10 minutes. Thereafter the solution was subjected to centrifugation at 3,000 G for 10 minutes using a centrifuge, Tomy CD100R (Tomy Seiki Co. in Japan)

9) The supernatant was collected and cooled on ice, and then subjected to centrifugation at 4° C. (at 10,000 G for 10 minutes.)

10) The supernatant was collected and neutralized to pH 7 with about 3.6 ml of 10N sodium hydroxide, and the neutralized solution was concentrated using an ultrafilter (Toyo Roshi UHP-150, Filter:UK-10, N$_2$ pressure: 4.0 kg/cm$^2$)

11) The resulting concentrate (60 ml) was subjected to gel filtration (buffer: 10 mM Tris-HCl/10 mM NaCl (pH7.5), flow speed: 60 ml/h.) to collect 20 ml fractions using Sepharose 6B column (manufactured by Pharmacia Inc., column size: 5 cm (i.d.)×100 cm (2 l)).

12) The 43rd to 56th fractions were combined to prepare 280 ml of a solution followed by addition of 450 μg of Pronase E (Kaken Kagaku Co. in Japan) and warmed at 37° C. for 2 hours while shaking. Thereafter the mixture was concentrated using an ultrafilter (Toyo Roshi UHP-62, filter: UK-10, N$_2$ pressure: 4.0 kg/cm$^2$). Then the concentrate was subjected to anion exchange chromatography using FPLC system (manufactured by Pharmacia Inc., column: mono Q HR 10/10). That is, the sample was applied to the column using a buffer solution containing 10 mM Tris-HCl (pH7.5) and 10 mM of NaCl, and then the column was washed with 200 ml of the same type buffer solution as the above but containing an increased amount 165 mM of NaCl. Then, totally 400 ml of the eluate was used to elute the object LPS while increasing the NaCl concentration so that the NaCl concentration gradient ranges from 165 mM to 1M. Two ml fractions were collected. The 5th to 8th fractions after the start of the concentration gradient which were confirmed to be positive to the limulus test were combined to yield 8 ml of LPS of about 92% purity (LPS: 3.03 mg (in terms of E. coli LPS according to the limulus test; the same applies to the following), sugar: 0.23 mg, protein: 0.04 mg)

13) Then, the 8 ml was subjected to gel filtration (buffer: water) using Sephadex G-25 (column: 2.0 cm (i.d.)×20.2 cm (66 ml)) to collect 3 ml fractions. The 9th to 12th fractions confirmed to be positive to the limulus test were combined to yield 12 ml of glycolipid of about 95% purity (LPS: 2.7 mg, sugar: 0.18 mg, protein: 0.03 mg). The sugar content was determined according to the phenol-sulfuric acid method, while the protein content, according to the Lowry method. Here, the combined fractions were confirmed to be acidic by anion exchange chromatography. The molecular weight according to SDS electrophoresis was 6,000–10,000.

14) The above fractions were frozen at $-80°$ C., and then lyophilized to a constant weight which was measured to be 0.75 mg. Hereunder, this lyophilized sample is referred to as wheat LPS only.

The limulus activity of wheat LPS was determined to be 2.7 mg according to the method described in Experiment 1 given later, so its specific activity is calculated to be 3.6 (2.7÷0.75). Here, the foregoing purification procedures are supposed to have removed substantially all the independent sugars present as contaminants, so all the sugars detected are supposed to be those constituting the wheat LPS. Thus, the purity of the wheat LPS on the basis of weight at this stage may be calculated as follows:

Protein content: 0.03 mg
LPS content: 0.72 mg (0.75−0.03)
Purity=0.72÷0.75×100=96 (%)

Physical properties of wheat LPS

15) Molecular weight

Wheat LPS was dissolved in distilled water to prepare a 1 mg/ml solution of CHF, and 4 μl of the solution was placed in a 1.5 ml Treff tube. Separately, 2.5% of SDS, 5% of mercaptoethanol and 10 mM Tris-HCl (pH 8.0) were added to 1 mM EDTA to prepare 1 μl of an SDS treatment solution, and this solution was added to the above solution in the Treff tube which was then dipped in boiling water for 3 minutes. Phast System of Pharmacia Inc. was used in the electrophoresis experiments. That is, one μl of the mixture was applied to a gel (Phast Gel Gradient 8–25 of Pharmacia Inc.) which was connected to the electrodes through SDS-Buffer Strip of Pharmacia Inc., the maximum potential difference and the maximum electric current were set to 250 v and 10 mA, respectively, and then the electrophoresis started. Throughout the specification and the claims, this type electrophoresis is called SDS electrophoresis. At the end of the electrophoresis, the behaviors in Coomassie staining and silver staining were observed.

For Coomassie staining, Phast Gel Blue R was used as the staining solution, and a mixture of methanol, acetic acid and distilled water (volumetric ratio is 3:1:6), as the decoloring solution. The staining and decoloring were carried out in the following order:
1) Stained at 50° C. for 8 minutes.
2) Stained at 50° C. for 5 minutes.
3) Stained at 50° C. for 8 minutes.
4) Decolored at 50° C. for 10 minutes.
5) Protected at 50° C. for 5 minutes (a mixture of glycerol, acetic acid and distilled water in a volumetric ratio of 5:10:85).
6) Dried.

The silver staining was carried out in the following order:
1) Treated with a wash (a mixture of ethanol, acetic acid and distilled water in a volumetric ratio of 5:1:4) at 50° C. for 2 minutes.
2) Treated with a wash (a mixture of ethanol, acetic acid and distilled water in a volumetric ratio of 10:5:85) at 50° C. for 2 minutes.
3) Treated with a wash (a mixture of ethanol, acetic acid and distilled water in a volumetric ratio of 10:5:85) at 50° C. for 4 minutes.
4) Treated with a sensitizer solution (8.3% glutar dialdehyde) at 50° C. for 6 minutes.
5) Treated with a wash (a mixture of ethanol, acetic acid and distilled water in a volumetric ratio of 10:5:85) at 50° C. for 3 minutes.
6) Treated with a wash (a mixture of ethanol, acetic acid and distilled water in a volumetric ratio of 10:5:85) at 50° C. for 5 minutes.
7) Treated with a wash (deionized water) at 50° C. for 2 minutes.
8) Treated with a wash (deionized water) at 50° C. for 2 minutes.
9) Treated with 0.25 w/v % of silver nitrate at 40° C. for 13 minutes.
10) Treated with a wash (deionized water) at 30° C. for 30 seconds.
11) Treated with a wash (deionized water) at 30° C. for 30 seconds.
12) Treated with a developer (0.04 v/v % of formaldehyde+2.5 w/v % of sodium carbonate as a wash) at 30° C. for 30 seconds.
13) Treated with a developer (0.04 v/v % of formaldehyde+2.5 w/v % of sodium carbonate as a wash) at 30° C. for 4 minutes.
14) Treated with a reaction termination solution (5 v/v % of acetic acid) at 50° C. for 2 minutes.
15) Treated with a protective solution (a mixture of acetic acid, glycerol and distilled water in a volumetric ratio of 10:8:85) at 50° C. for 3 minutes.
16) Dried.

LPS are subjected to silver staining, but not to Coomassie staining. This difference was taken into consideration to observe the stained bands, and the main stained band of wheat LPS was found at a position indicating a molecular weight of 8,000±1,000.

16) Phosphorus content

The captioned content was determined as follows according to the Chen-Toribara method (Chen et al., *"Analytical Chemistry"*, vol. 28 pp. 1756–1758, 1956)

Wheat LPS was dissolved in distilled water to prepare 20 μl of a solution containing 25 μg of wheat LPS which was then placed in a small test tube. To the mixture there was added 20 μl of 50 v/v % perchloric acid, and then the mixture was heated on a gas burner for 1 minute to ash. Thereafter, 0.5 ml of distilled water and then 0.5 ml of a reaction reagent (a portion of the preparation made by mixing 1 ml of 6N sulfuric acid, 2 ml of distilled water, 2 ml of 2.5 v/w % ammonium molybdate and 1 ml of 10 v/w % of ascorbic acid) were added to the heated mixture which was then allowed to stand for 30 minutes at room temperature. Thereafter the absorption at 820 nm ($OD_{620nm}$) was determined. Here, as the standard sample for the preparation of the calibration curve, potassium dihydrogen phosphate (manufactured by Wako Jun-yaku Co. in Japan) was diluted with water to prepare 0.5 ml of solutions containing 2.5 μg, 1 μg, 0.25 μg or 0 μg of the standard in terms of phosphorus. In this connection, 1 g of phosphorus corresponds to 4.39 g of potassium dihydrogen phosphate. The effects observed are shown in Table 1 given below.

TABLE 1

| OD 820 nm | Samples |
|---|---|
| | Potassium dihydrogen phosphate (in terms of phosphorus; μg) |
| 0.002 | 0 |
| 0.150 | 0.25 |
| 0.620 | 1.0 |
| 1.559 | 2.5 |
| | Wheat LPS (data of four samples) (content of phosphorus calculated considering calibration curve; μg) |
| 0.036 | 0.1 |
| 0.073 | 0.2 |
| 0.104 | 0.3 |
| 0.139 | 0.4 |

Note:
The data of wheat LPS are modified by subtracting the values of the control not subjected to the heating from the observed values in order to avoid occurrence of errors due to mixing-in of inorganic phosphorus from, for example, phosphate buffer solution.

On the assumption that the molecular weight of wheat LPS is 8,000, the number of phosphorus in LPS is calculated to be 1–4 per mol. according to the following equation on the basis of the data shown in the above table.

$$\text{Phosphorus content} \times 10^{-6} \times \frac{\text{Molecular weight}}{25 \times 10^{-6}} \times \frac{1}{32}$$

For an explanation as to why the number of phosphorus ranged from 1 to 4, one may guess that the phosphoric acid (s) may be eliminated due to the mixing-in of the monophosphoesterase in the purification stage. In view of this, it may be right to conclude that wheat LPS has not less than 1 phosphorus per mol.

17) Hexosamine content

The captioned content was determined as follows according to the Elson-Morgan method (Library of biochemical experiments, No. 4, pp. 377–379, Tokyo Kagaku Dojin Shuppan Co. in Japan).

Wheat LPS was dissolved in distilled water to prepare a solution containing 1 mg/ml of wheat LPS, and its 100 μl portion as placed in a test tube with a screwcap (manufactured by Iwaki Glass Co. in Japan) followed by addition of 100 μl of 8N HCl thereto, and the mixture was heated at 110° C. for 16 hours, and then about 200 μl of 4N NaOH was added to the mixture to bring the pH to 7. A 100 μl portion of the mixture was separated off and placed in another test tube with a screwcap followed by addition of 200 μl of Reagent A explained below thereto. The mixture was then heated at 105° C. for 1.5 hours, and then cooled with a running water. Next, a 100 μl portion of the mixture was separated off followed by addition of 670 μl of a 96% ethanol and then 67 μl of Reagent B explained below, and was then allowed to stand at room temperature for 1 hour followed by determination of adsorption at 535 nm. As the standard sample to prepare the calibration curve, 0.20–200 μg/ml of N-acetyl glucosamine (Wako Jun-yaku Co. in Japan) was used. Reagent A: prepared by mixing 75 μl of acetyl acetone and 2.5 ml of 1.25N sodium carbonate Reagent B: prepared by mixing 1.6 g of p-dimethyl benzaldehyde, 30 ml of conc. hydrochloric acid and 30 ml of 96% ethanol As a result, the number of the hexosamine in wheat LPS was 6±2 per mol. on the assumption that its molecular weight is 8,000.

17) Fatty acid content

To 90 μl of a solution of wheat LPS in distilled water containing 1 mg/ml of wheat LPS there was added 10 μl of an internal standard (0.55 mM margaric acid) followed by addition of 1.0 ml of 0.5M sodium methylate for hydrolysis and esterification of fatty acid esters. The mixture was allowed to stand at room temperature for 1 hour followed by the addition of 960 μl of 0.5N HCl thereto for neutralization. Two ml of hexane was added to the mixture which was then stirred vigorously for 15 minutes. Next, the resulting mixture was subjected to centrifugation at 1,000 G for 5 minutes to separate off the hexane layer. The hexane was evaporated off by nitrogen gas, and the layer was concentrated to about 20 μl. The resulting concentrate was subjected to gas chromatography (GC8A-PF manufactured by Shimazu Co. in Japan; capillary column: FSCAP Sp2330 manufactured by Spelco Co. in Canada; carrier gas: nitrogen) to determine the fatty acid content. As the standard for determination of the fatty acid content, there was used E. coli type LA-15-PP, a synthetic lipid A manufactured by Dai-ichi Kagaku Yakuhin Co. in Japan and known to have a molecular weight of 2,000 and a fatty acid count of 6 per mol.

As a result, the number of the fatty acid in wheat LPS was 6±2 per mol. on the assumption that its molecular weight is 8,000.

Figure 2:
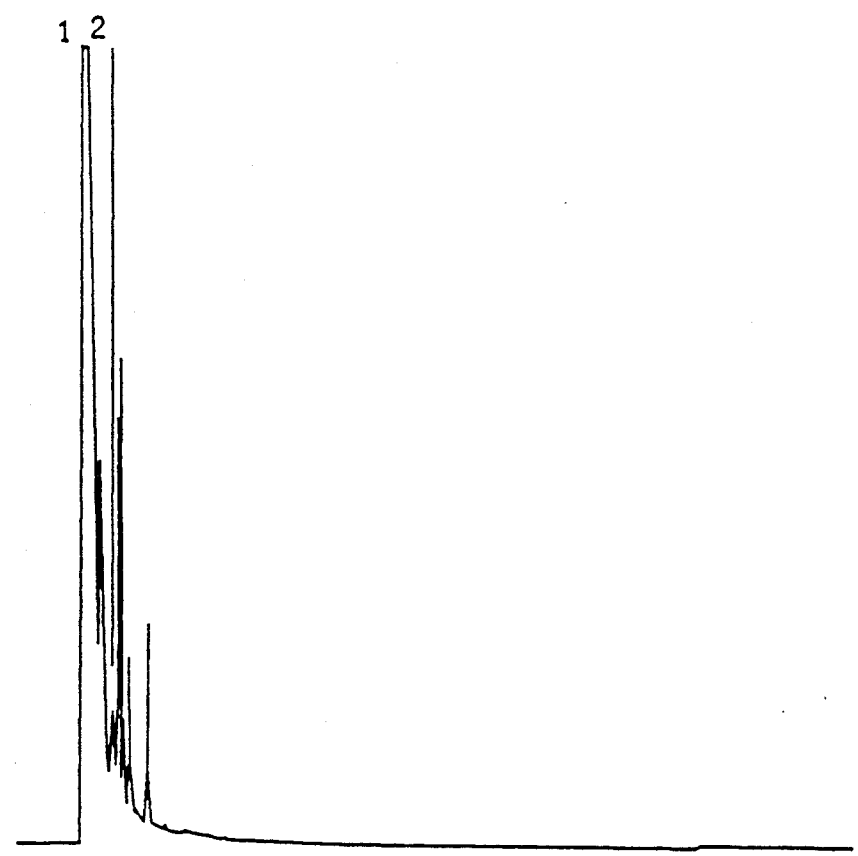
FIG. 2 is a gas chromatographic chart of E. coli LPS, showing the peaks evidencing the presence of fatty acids therein.
Figure 3:
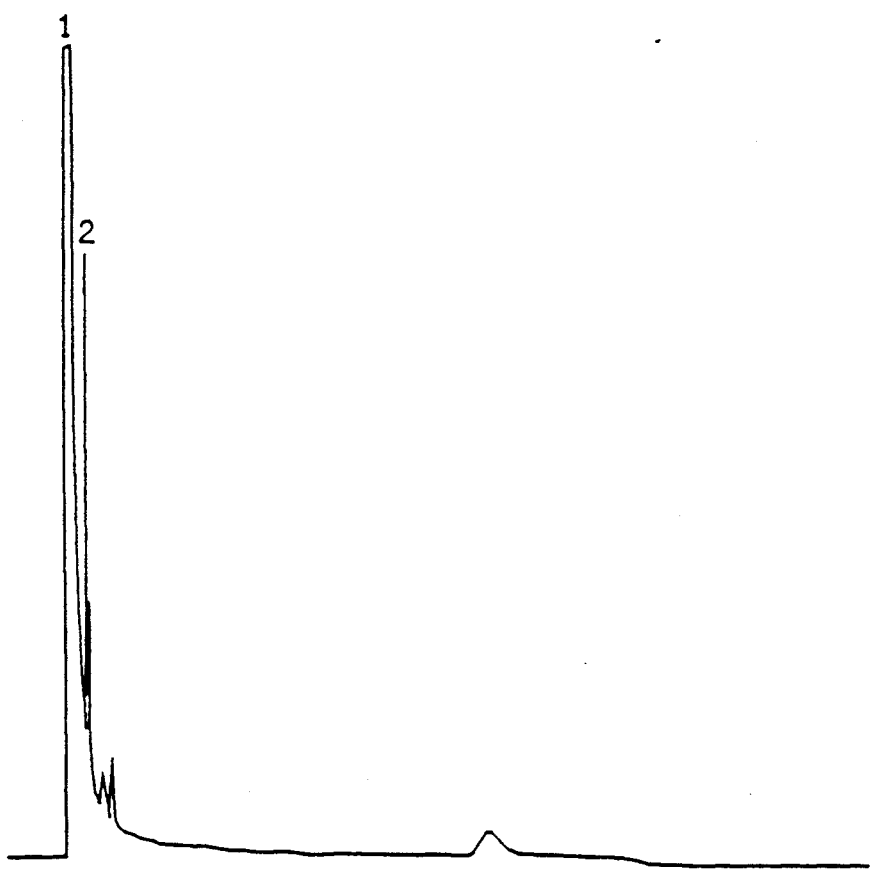
FIG. 3 is a gas chromatographic chart of B. pertussis LPS available for use according to the present invention, showing the peaks evidencing the presence of fatty acids therein.

The charts observed in the above gas chromatography are shown in accompanying FIGS. 1–3. FIG. 1 is the chart of wheat LPS, FIG. 2 is that of E. coli LPS, and FIG. 3 is that of B. pertussis LPS.

Figure 4:
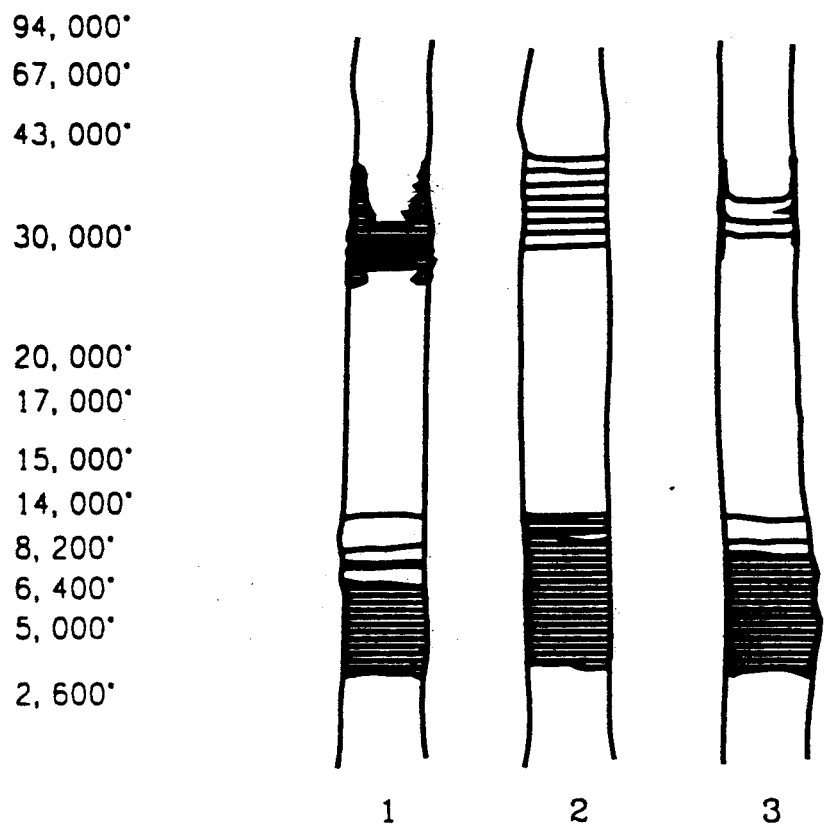
FIG. 4 is a chart showing the patterns of the LPSs of the present invention on SDS-PAGE method.

The retention times (minutes) corresponding to the main peaks shown in FIGS. 2–4 are as follows:

| | No. of peak | Retention time (min.) |
|---|---|---|
| FIG. 2: | 1 | 2.450 |
| | 2 | 2.758 |
| FIG. 3: | 1 | 2.417 |
| | 2 | 2.742 |
| FIG. 4: | 1 | 2.433 |
| | 2 | 3.028 |

By the comparison of FIGS. 1–3, it is apparent that wheat LPS and E. coli LPS show similar charts, whereas the chart of wheat LPS is clearly different from that of B. pertussis LPS.

18) KDO content

The KDO content was determined as follows on the basis of the diphenylamine method (Shaby R. et al., "Analytical Biochem.", 58(1), pp. 123–129, 1974).

A KDO detection reagent was prepared by combining 500 mg of dipenylamine, 5 ml of ethanol, 45 ml of glacial acetic acid and 50 ml of conc. hydrochloric acid (all commercially available from Wako-junyaku Co. in Japan). A 500 μl portion of the prepared reagent was combined with 250 μl of distilled water containing 1.05 mg/ml of wheat LPS. The resulting mixture was heated in a boiling water bath at 100° C. for 30 minutes and then cooled in cooling water at 23° C. for 30 minutes.

The UV absorption of the mixture was determined at 420, 470, 630 and 650 nm to provide data $A_{420}$, $A_{470}$, $A_{630}$ and $A_{650}$, respectively. As the standard sample, there was used 250 μl of distilled water containing 127 μg/ml of ammonium salt of KDO (Sigma Co. in U.S.A.). The value S for the test and standard samples was calculated according to the following equation:

$$S = A_{420} - A_{470} + A_{630} - A_{650}$$

The value of the test sample ($S_t$) was 0.379, whereas that of the standard sample ($S_s$) was 0.294. The comparison of the two values suggests that wheat LPS contains 5±1 mol. on the assumption that its molecular weight is 8,000.

REFERENCE EXAMPLE 2

(preparation of chlorella LPS)

1) Thirty grams of cell membrane-crushed chlorella (Mannan-foods YS Co. in Japan) was washed with ethanol until the wash was not colored green any more.

2) The residue (26 g) was dissolved in distilled water to prepare a 100 mg/ml solution which was then shaken at 45° C. for 2 hours followed by centrifugation (4° C. 10,000 G for 30 min.).

3) The supernatant was filtered through Toyo-roshi No. 2 followed by extraction with distilled water.

4) The extracts (290 ml) were subjected to anion exchange chromatography under the following conditions:
Column: Q Sepharose (φ3 cm×23 cm. volume: about 180 ml)
Buffer: 10 mM Tris-HCl (pH 7.5)
Gradient of NaCl conc.: 10 mM, 400 mM, 1M
Flow rate: 100-200 ml/hr.
Temperature: Room temperature 5) The eluate (310 ml) was treated with glucoamylase at pH 5.0, 40° C., for about 2 hrs. to decompose the starch. The decomposition of the starch was confirmed by the fact that the coloring of the solution was not found in the starch iodide reaction.

6) The solution was subjected to centrifugation (10,000 G for 10 min.) to collect the supernatant which was then nuetralized with a 10N NaOH solution to pH 7 followed by ultrafiltration using a ultrafilter having a pore size which excludes matter having a molecular weight of 20,000 or more.

7) The thus prepared concentrate (30 ml) was subjected to anion exchange chromatography using FPLC system (column: mono Q HR 10/10). That is, the sample was applied to the column using a buffer solution containing 10 mM Tris-HCl (pH 7.5) and 10 mM of NaCl, and then the column was washed with 200 ml of the same type buffer solution as the above but containing an increased amount 165 mM of NaCl. Then, totally 400 ml of the eluate was used to elute the object LPS while increasing the NaCl concentration so that the NaCl concentration gradient ranges from 165 mM to 1M. Two ml fractions were collected. The 5th to 8th fractions after the start of the concentration gradient which were confirmed to be positive to the limulus test were combined.

8) Then, a 8 ml portion of the fractions was subjected to gel filtration (buffer: water) using Sephadex G-25 (column: 2.0 cm (i.d. )×20.2 cm (66 ml)) to collect 3 ml fractions. The 9th to 12th fractions confirmed to be positive to the limulus test were combined to yield a 12 ml solution (LPS: 14.3 mg, sugar: 2.0 mg, protein: 0.53 mg). The LPS content was determined by the procedure as described in Experiment 1 mentioned later, the sugar content was determined according to the phenol-sulfuric acid method, and the protein content, according to the Lowry method.

9) The above fractions were frozen at −80° C., and then lyophilized to a constant weight which was measured to be 5.8 mg. Hereunder, this lyophilized sample is referred to as chlorella LPS.

The limulus activity of chlorella LPS corresponds to 14.3 mg, so its specific activity is calculated to be 2.5 (14.3÷5.8).

The foregoing purification procedures are supposed to have removed substantially all the independent sugars present as contaminants, so all the sugars detected are supposed to be those constituting chlorella LPS. Thus, the purity of chlorella LPS on the basis of weight at this stage may be calculated as follows:
Protein content: 0.53 mg
LPS content: 5.27 mg (5.8-0.53)
Purity=91 (%) (5.27÷5.8×100)

Physical properties of chlorella LPS

Following the procedures as described in Reference Example 1, the captioned properties were determined as follows (only the molecular weight was determined by SDS-PAGE method described in Reference Example 4):
Molecular weight: 40,000-90,000
Phosphorus content: 4±1 per molecular weight of 10,000
Hexosamine content: 7±1 per molecular weight of 10,000
Fatty acid content: 6±1 per molecular weight of 10,000
KDO content: 2±1 per molecular weight of 10,000

REFERENCE EXAMPLE 3

(preparation of B. pertussis LPS)

An experimental B. pertussis solution obtained from Serum Laboratory, a public institute of Chiba prefecture in Japan (2.0×10^{10} cells/ml) was used.

The solution was suspended in sterile water to prepare a suspension containing 25 mg (dry basis)/ml of dead cells. To the suspension, there was added an equivalent of a 90% hot phenol solution (68°-70° C.) was added, and the mixture was shaked at 68° C. for 1 hr. The mixture was subjected to centrifugation at 8,000 G, 4° C. for 20 min. to collect the aqueous layer. Sterile water in the same quantity as of the aqueous layer was added to the remaining phenol, and the mixture was shaked in the same manner as the above. The resulting aqueous layer was combined with the first aqueous layer followed by dialysis in running water overnight, and then the mixture was concentrated to a tenth using a rotary evaporator. The concentrate was subjected to centrifugation at 8,000 G, 4° C. for 20 min. The supernatant was separated off, and a small amount of sodium acetate was added thereto. Cold ethanol at 0°-4° C. was added to the mixture in an amount of six times as much as the latter, and the resulting mixture was allowed to stand at −20° C. overnight. Then the mixture was subjected to centrifugation at 4,000 G, 4° C. for 30 min. to collect the sediment which was subjected to centrifugal washing with ethanol (twice) and acetone (once) followed by drying with an aspirator. The residue was suspended in distilled water to prepare a 20 mg/ml of solution which was then subjected to ultrasonic treatment with a Sonifia 185 (Branson Co. in U.S.A.) (outlet control 5, 15 min., room temperature). The solution was subjected to centrifugation at 2,500 G, 4° C. for 10 min. to separate off the supernatant.

The supernatant was treated at 4° C. with nucleases, DNase I and Rnase A (both manufactured by Sigma Co. in U.S.A) for 15-16 hrs; totally 10 μg/ml of DNase I and 20 μg/ml of Rnase A were used. The same amount of the nucleases as the above were added to the mixture followed by warming at 37° C. for 2 hrs and centrifugation at 2,500 G, 4° C. for 10 min. to separate off the supernatant.

The supernatant was filtered through a pore size of 0.2 μm using Acrodisc manufactured by Gelman Co. in U.S.A. The filtrate was subjected to molecular sieve (resin: Sepharose 6B manufactured by Pharmacia Co. in U.S.A; column size: 5 cm (i.d.)×100 cm (length); buffer: 10 mM of Tris-HCl/10 mM of NaCl (pH 7.5); flow rate: about 3 ml/cm²/hr.). The fractions confirmed to be positive to limulus test with LS-1 kit commercially available from Sei-Kagaku Kogyo Co. in Japan were collected and filtered through a pore size of 0.2 μm using Acrodisc mentioned above. The filtrate was subjected to ion exchange (apparatus: FPLC manufactured by Pharmacia in U.S.A.; resin: mono Q HR 10/10 manufactured by Pharmacia in U.S.A.; buffer: 10 mM of Tris-HCl/10 mM of NaCl (pH 7.5); flow rate: 2 ml/min.) wherein the filtrate was washed with the buffer for 15 min., then, after the NaCl content of the buffer was increased to 165 mM, for 30 min., then, for 20 min. while increasing the NaCl content to provide a NaCl content gradient from 165 mM to 1M, and then, for 30 min. at the NaCl content of 1M. The fractions confirmed to be positive to limulus test with LS-1 kit commercially available from Sei-Kagaku Kogyo Co. in Japan were collected.

The collected fractions were combined and desalted on a column (resin: Sephadex G-25 fine manufactured by Pharmacia in U.S.A.; column size: 2 cm (i. d.)×25 cm (length); eluting agent: distilled water), and then lyophilized.

Nucleic acid is of the greatest possibility of being mixed in the lyophilized sample (4.50 mg). Therefore, the UV absorption curve (200-400 nm) was prepared, and the absorbance at 60 nm was determined. The nucleic acid content was calculated to be 1% or less on the basis of the above absorbance in view of the fact that the nucleic acid content was 50 μg/ml in the case where the absorbance was 1. In addition, no apparent evidence showing the presence of a protein was observed in SDS electrophoresis. Thus, considering the detection sensibility, the highest content of proteins which may be mixed in the above lyophilized sample was estimated to be 0-3%. Accordingly, the purity of the above lyophilized sample was estimated to be 96% or more.

The physical properties of the thus prepared *B. pertussis* LPS were determined in the same manner as described in Reference Example 1, but the only molecular weight was determined by the SDS-PAGE method described in Reference Example 4. The results were as follows:

Physical properties of *B. pertussis* LPS

Molecular weight: 6,000±1,000
Phosphorus content: 4 per molecular weight of 6,000
Hexosamine content: 12 per molecular weight of 6,000
Fatty acid content: 4 per molecular weight of 6,000
KDO content: 2±1 per molecular weight of 6,000

The physical properties of *E. coli* LPS (0128: B8 manufactured by Difco Co. in U.S.A.) determined in the same manner as described in Reference Example 1 were as follows (the only molecular weight was determined by the SDS-PAGE method described in Reference Example 4):

Physical properties of *E. coli* LPS

Molecular weight:
  40,000±10,000
  8,000±4,000
Phosphorus content: 12 per molecular weight of 30,000
Hexosamine content: 45±6 per molecular weight of 30,000
Fatty acid content: 18 per molecular weight of 30,000
KDO content: 5±1 per molecular weight of 30,000

REFERENCE EXAMPLE 4

1) In a 50 ml coning tube, there was charged 1.04 g of hard flour containing 1.09% of ash (1 Canadian wheat from Canada) followed by addition of 20 ml of distilled water thereto to prepare a 50 mg/ml aqueous solution of wheat flour.

2) The solution was cultured in a water bath at 37° C. while shaking, and 0.5 ml portions of the solution were collected at 0, 1, 2, 3, 4, 6, 8, 10, 12, 20, 24 and 45 hours thereafter. 100 μl portions of the respective solutions diluted to 1 to 100,000 times were taken in standard agar culture media available from Nissui Seiyaku Co. in Japan and having the following composition to determine the number of living cells and to observe the colonies.

Standard agar culture media (Nissui Seiyaku's code No.: 05618)

Yeast extracts: 2.5 g/l
Peptone: 5.0 g/l
Glucose: 1.0 g/l
Agar: 15.0 g/l
pH: 7.1±0.1

At the end of 8 and 10 hour culture, yellow to creamy opaque colony (colony 1), creamy opaque colony (colony 2) yellow translucent colony (colony 3), milk white opaque colony (colony 4), and white opaque small colony (colony 5), which were judged to be different from each other, were scattered on the respective standard agar culture having the same composition as the above, for subcultivation. The gram staining and limulus activity of the bacteria in the colonies were determined.

Here, the "limulus activity" means to be positive to limulus test which is a method invented by Levin in 1968 for quantitative determination of endotoxin using a norseshoe crab haemocyte extract and a chromogenic substrate. The limulus test is known as a method for the detection of LPSs, and may be carried out using, for example, a reagent set commercially available from Sei-Kagaku Kogyo Co. in Japan under the trade name of Toxi Color system.

Of the above colonies, the limulus activity of the colonies 4 and 5 (both being gram stain-positive) were extremely low as compared with that of the colonies 1, 2 and 3 (all being gram stain-negative), so the former colonies were taken aside. The morphological and biochemical characteristics of only the colonies 1, 2 and 3 were observed using the media available from NIssui Seiyaku Co. and ID tests EB-20 to show the following results:

Bacteria forming the colony 1 (ID number: 900814-1)

(The bacteria were deposited with Fermentation Research Institute Agency of Industrial Science and Technology on Aug. 17, 1990 under the number of FERM P-11664 and transferred to the international deposit under BUDAPEST TREATY on Aug. 12, 1991 under the number of FERM BP-3509.)

The bacteria are supposed to belong to the genus Serratia of the family Enterobacteriaceae in view of the following morphological and biochemical characteristics.

a) Morphological characteristics
   1) Small rod
   2) No Motility
   3) Gram stain:
b) Growth
   1) Standard agar medium: a yellow to creamy round opaque colony is formed.
   2) SS agar medium: A white translucent colony is formed.
   [SS agar medium: Nissui Seiyaku's code No. 05031]
      Broth: 5.0 g/l
      Bile acid salts: 9.0 g/l
      Peptone: 7.5 g/l
      Lactose: 10.0 g/l
      Sodium citrate: 8.5 g/l
      Sodium thiosulfate: 5.5 g/l
      Ferric citrate: 1.0 g/l
      Neutral red: 0.025 g/l
      Brilliant green: 0.033 g/l
      Agar: 13.5 g/l
      pH: 7.1±0.1
   3) TSI agar medium: No change is found on the slant, but the higher layer changes to yellow. Gas if produced.
   [SS agar medium: Nissui Seiyaku's code No. 05031]
      Broth: 5.0 g/l
      NaCl: 5.0 g/l
      Peptone: 15.0 g/l
      Lactose: 10.0 g/l
      Sucrose: 10.0 g/l
      Glucose: 1.0 g/l
      Ferric citrate: 0.2 g/l
      Sodium thiosulfate: 0.2 g/l
      Phenol red 0.02 g/l
      Agar 15.0 g/l
      pH: 7.6±0.1
c) Physiological characteristics
   1) Voges-Proskauer reaction: +
   2) Indole production: —
   3) Hydrogen sulfide production: —
   4) Utilization of citrate: +
   5) Urease: —
   6) Oxidase: —
   7) O-F test: +
d) Utilization of carbon sources
   1) Lactose: +
   2) Adonitol: —
   3) Rhamnose: +
   4) Mannitol: +
   5) Esculin: +
   6) Inositol: —
   7) Sorbitol: +
   8) Arabinose: +
   9) Raffinose: +
   10) Sucrose: +
e) Others
   1) Lysin decarboxylase: —
   2) Utilization of malonate: —
   3) Arginine dihydroxylase: —
   4) Phenylalanine deaminase: —
   5) Ornithine decarboxylase: —

Bacteria forming the colony 2 (ID number: 900814-2)
(The bacteria were deposited with Fermentation Research Institute Agency of Industrial Science and Technology on Aug. 17, 1990 under the number of FERM P-11665 and transferred to the international deposit under BUDAPEST TREATY on Aug. 12, 1991 under the number of FERM BP-3510.)

The bacteria are supposed to belong to the genus Enterobacter of the family Enterobacteriaceae in view of the following morphological and biochemical characteristics.

a) Morphological characteristics
   1) Small rod
   2) No Motility
   3) Gram stain: —
b) Growth
   1) Standard agar medium: a creamy opaque colony is formed.
   2) SS agar medium: A red opaque colony is formed.
   3) TSI agar medium: No change is found on the slant, but the higher layer changes to yellow. Gas if produced.
c) Physiological characteristics
   1) Voges-Proskauer reaction: +
   2) Indole production: —
   3) Hydrogen sulfide production: —
   4) Utilization of citrate: +
   5) Urease: —
   6) Oxidase: —
   7) O-F test: +
d) Utilization of carbon sources
   1) Lactose: +
   2) Adonitol: —
   3) Rhamnose: +
   4) Mannitol: +
   5) Esculin: +
   6) Inositol: —
   7) Sorbitol: +
   8) Arabinose: +
   9) Raffinose: +
   10) Sucrose: +
e) Others
   1) Lysin decarboxylase: —
   2) Utilization of malonate: +
   3) Arginine dihydroxylase: +
   4) Phenylalanine deaminase: —
   5) Ornithine decarboxylase: +

Bacteria forming the colony 3 (ID number: 900814-3)
(The bacteria were depositted with Fermentation Research Institute Agency of Industrial Science and Technology on Aug. 17, 1990 under the number of FERM P-11666 and transferred to the international deposit under BUDAPEST TREATY on Aug. 12, 1991 under the number of FERM BP-3511.)

The bacteria are supposed to belong to the genus Pantoea of the family Enterobacteriaceae in view of the following morphological and biochemical characteristics.

a) Morphological characteristics
   1) Small rod
   2) No Motility
   3) Gram stain: —
b) Growth
   1) Standard agar medium: A yellow round translucent colony is formed.

2) SS agar medium: No colony is formed.
3) TSI agar medium: No change is found on the slant, but the higher layer changes to yellow. Gas in not produced.
c) Physiological characteristics
  1) Voges-Proskauer reaction: +
  2) Indole production:
  3) Hydrogen sulfide production: −
  4) Utilization of citrate: +
  5) Urease: −
  6) Oxidase: −
  7) O-F test: +
d) Utilization of carbon sources
  1) Lactose: +
  2) Adonitol: −
  3) Rhamnose: +
  4) Mannitol: +
  5) Esculin: +
  6) Inositol: −
  7) Sorbitol: +
  8) Arabinose: +
  9) Raffinose: −
  10) Sucrose: +
e) Others
  1) Lysin decarboxylase: −
  2) Utilization of malonate: +
  3) Arginine dihydroxylase: −
  4) Phenylalanine deaminase: −
  5) Ornithine decarboxylase: −

4) The colonies 1, 2 and 3 were transferred to 1 liter L-broth medium, respectively, and the media were shaken at 37° C. over night, and then subjected to centrifugation at 5,000 G, 4° C. for 20 minutes to collect the cells. The L-broth was prepared by dissolving 10 g of polypeptone (Difco Co.), 5 g of yeast extracts (Difco Co.) and special grade NaCl (Wako-Jun-Yaku Co. in Japan) in distilled water, adjusting the pH of the solution to 7.5 with NaOH followed by autoclaving, and then adding a 400-fold dilent of a 40% solution of special grade glucose (Wako-Jun-Yaku Co.) to the solution.

5) The cells of the respective colonies were suspended in 50 ml of distilled water, and 50 ml of a 90% hot phenol was added to the suspension followed by stirring at 65°-70° C. for 20 minutes. After being cooled, the mixture was subject to centrifugation at 10,000 G, 4° C. for 20 minutes to recover the aqueous layer. The phenol layer was treated additional two times in the same manner as the above. The combined three aqueous layers were subjected to dialysis overnight to remove the phenol. The inner solution was subjected to ultrafiltration using UK-20 (Advantec Toyo Co.) for concentration by cutting off molecular weight 200,000; $N_2$ pressure: 2 atms.

6) The concentrated sample was subjected to anion-exchange chromatography using Q-Sepharose Fast Flow (Pharmacia Co.). That is, the sample was applied to the column using a buffer solution containing 10 mM Tris-HCl (pH 7.5) and 10 mM of NaCl, and then the limulus active fractions were eluted with 400 mM NaCl/10 mM Tris-HCl (pH 7.5). The eluate was subjected to ultrafiltration unde the same conditions as the above for desalting and concentration to produce 96% or more pure LPS. The nucleic acid was eluted with 1M NaCl/10 mM Tris-HCl (pH 7.5).

The results of the respective cells are shown in Tables 2–4. Here, the LPS content is in terms of E. coli LPS. The sugar content was determined according to the phenol-sulfuric acid method (M. Dubis et al., "Analytical Chemistry", vol. 28, p. 350, 1956), while the protein content was determined by the Lowry method (O. H. Lowry et al., "Journal of Biological Chemistry), vol. 193, p. 65, 1951. The nucleic acid content was determined on the basis of the measurements of OD at 260 nm (1 OD=50 μg), and the purity (%) was calculated by the equation:

$$\text{Purity} = \frac{\text{Dried yield} - (\text{Protein yield} + \text{nucleic acid yield})}{\text{Dried yield}} \times 100$$

Table 2: 900814-1

Total dried yield (mg): 6.8
LPS (mg): 19.8
Sugar (mg): 3.1
Protein (μg): 86
Nucleic acid (μg): <161
Purity (%): 96<

Table 3: 900814-2

Total dried yield (mg): 10.4
LPS (mg): 75.6
Sugar (mg): 2.5
Protein (μg): 64
Nucleic acid (μg): <108
Purity (%): 98<

Table 4: 900814-3

Total dried yield (mg): 19.2
LPS (mg): 103.6
Sugar (mg): 7.6
Protein (μg): 73
Nucleic acid (μg): <137
Purity (%): 99<

6) Molecular weight

The LPSs resulting from the respective cells were dissolved in distilled water, respectively to prepare solutions containing 2 mg/ml of LPSs. The 10 μl portions of the solutions were placed in 1.5 ml plastic tubes. To the respective portions there was added 10 μl of an SDS treatment solution prepared by mixing 10 μl of 10% (w/v) of SDS, 45 μl of 5% β-mercaptoethanol, 90 μl of a CBB coloring matter solution, 112.5 μl of 0.5M Tris-HCl (pH 6.8) and 22.5 μl of distilled water. The resulting mixture was mixed well and then immerssed in boiling water for 5 minutes, and immediately thereafter the mixture was quenched in ice water.

10 ml of 10% (w/v) SDS, 17.9 g of tricine and 3.03 g of Tris were dissolved in 1 liter of distilled water to prepare a buffer solution for electrophoresis which was then placed in Slab-gel electrophoresis tank (Marisoru Co.). 20% polyacrylamide gel was fixed in the tank, and the sample was placed in the sample groove. The voltage was kept at 50 v for 1 hour, and then at 150 v, and the electrophoresis was allowed to proceed until the coloring matter flowed out through the gel; these procedures are defined as SDS-PAGE method throughout the specification and the claims. At the end of the electrophoresis, silver staining was carried out using silver staining kit 161-0443 (Bio-rad Co.) at room temperature to confirm the behavior.

The molecular weight of the LPSs of the present invention was calculated to be 5,000±1,000 (LPS1 resulting from bacteria 900814-1), and 6,500±2,500 (LPS2 and LPS3 resulting from bacteria 900814-2 and 900814-3, respectively) in view of the behaviors of the markers for protein m. w. [Pharmacia's LMW kit E: phosphorirase b (94k), albumin (67k), ovalbumin (43k), carbonic anhydrase (30k)', trypsin inhibitor (20k), α-lactalbumin (14k)], and those of the markers for peptide m. w. [Pharmacia's 1860-101 m. w. marker: myoglobin (16.9k), myoglobin I and II (14.4k), myoglobin I (8.2k), myoglobin II (6.0k) and myoglobin IV (2.5k). In the same manner as the above, *E. coli* LPS (0127:B8LPS available from Difco Co.) was found to have dominant m. w. at 40,000±10,000 and 8,000±4,000.

The stained bands of LPS1, LPS2 and LPS3 in the silver staining are shown in FIG. 1. In FIG. 1, the number 1, 2 and 3 show the stained bands of LPS1, LPS2 and LPS3, respectively. As shown in FIG. 1, LPS1 showed another stained band around m. w. 30,000. LPS2 showed another stained band bridging from 30,000 to 43,000, but it may be said that it contains only little high molecular weight substance in view of the staining strength of the bands at 14,000 or less. Also in view of the sugar content and hexosamine content mentioned later, LPS2 the lowest sugar content, and LPS1 has higher sugar content than LPS3. This order is believed to be in harmony with the patterns observed in the electrophoresis. Further, the ratio of LPS content to total dried yield decreases in the order of LPS2, LPS3 and LPS1. Considering the foregoing, it may be estimated that LPS2 comprises relatively low molecular weight LPSs, and the content of low molecular weight LPSs decrease in the order of LPS3 and LPS1.

6) Phosphorus content

The captioned content was determined as follows according to the Chen-Toribara method (Chen et al., "Analytical Chemistry", vol. 28, pp. 1756-1758, 1956)

LPS1, LPS2 and LPS3 were dissolved in distilled water separately to prepare 20 μl solutions containing 31.6, 57.6, or 103.6 μg of LPS which were then placed in a small test tube. To the mixture there was added 20 μl of 50 v/v sulfuric acid followed by heating at 160° C. for 2 hours. Then 20 μl of 50 v/v % perchloric acid was added to the mixture which was then heated on a gas burner for 1 minute to ash. Thereafter, 0.5 ml of distilled water and then 0.5 ml of a reaction reagent (a portion of the preparation made by mixing 1 ml of 6N sulfuric acid, 2 ml of distilled water, 2 ml of 2.5 v/w % ammonium molybdate and 1 ml of 10 v/w % of ascorbic acid) were added to the heated mixture which was then allowed to stand for 30 minutes at room temperature. Thereafter the absorption at 820 nm ($OD_{820\ nm}$) was determined. Here, as the standard sample for the preparation of the calibration curve, potassium didrogen phosphate (manufactured by Wako Jun-yaku Co. in Japan) was diluted with water to prepare 0.5 ml of solutions containing 2.5 μg, 1 μg, 0.25 μg or 0 μg of phosphorus. In this connection, 1 g of phosphorus corresponds to 4.39 g of potassium didrogen phosphate. The effects observed are shown in Table 4 given below. In the table, the data of absorption are modified by subtracting the values of the control not subjected to the heating from the observed values in order to avoid occurrence of errors due to mixing-in of inorganic phosphorus from, for example, phosphate buffer solution. The P content (μg) is calculated on the basis of the data of absorption. The P content (w/w %) was calculated according to the following equation. In the equation, "0.67" is the OD value of 1 μg of the standard phosphorus, and the sample concentration is the proportion of the respective LPSs dissolved in distilled water (mg/ml).

$$P\ content\ (w/w\ \%) = \frac{Absorption\ of\ sample}{0.67 \times (sample\ concentration) \times 0.05}$$

P number is the number of phosphorus per m. w. 5,000 calculated according to the following equation:

$$P\ number = \frac{P\ content\ (w/w\ \%)}{100} \times \frac{5,000}{31}$$

TABLE 5

| LPS | Absorption | P content (μg) | P content (w/w %) | P number |
|---|---|---|---|---|
| 1 | 0.36 | 0.54 | 1.7 | 2 ± 1 |
| 2 | 0.31 | 0.46 | 0.8 | 1 ~ 2 |
| 3 | 0.87 | 1.30 | 1.3 | 2 ± 1 |

8) Hexosamine content

The captioned content was determined as follows according to the Elson-Morgan method (Library of biochemical experiments, No. 4, pp. 377-379, Tokyo Kagaku Dojin Shuppan Co. in Japan).

LPS was dissolved in distilled water to prepare a solution containing 1.58 mg/ml of LPS1, 2.88 mg/ml of LPS2 or 5.18 mg/ml of LPS3, and the respective 100 μl portions were placed in a test tube with a screwcap (manufactured by Iwaki Glass Co. in Japan) followed by addition of 100 μl of 8N HCl thereto, and the mixture was heated at 110° C. for 16 hours, and then about 200 μl of 4N NaOH was added to the mixture to bring the pH to 7. A 100 μl portion of the mixture was separated off and placed in another test tube with a screwcap followed by addition of 200 μl of Reagent A explained below thereto. The mixture was then heated at 105° C. for 1.5 hours, and then cooled with a running water. Next, a 100 μl portion of the mixture was separated off followed by addition of 670 μl of a 96% ethanol and then 67 μl of Reagent B explained below, and was then allowed to stand at room temperature for 1 hour followed by determination of adsorption at 535 nm. As the standard sample to prepare the calibration curve, 0.20-200 μg/ml of N-acetyl glucosamine (Wako Jun-yaku Co. in Japan) was used.

Reagent A: prepared by mixing 75 μl of acetyl acetone and 2.5 ml of 1.25N sodium carbonate Reagent B: prepared by mixing 1.6 g of p-dimethyl benzaldehyde, 30 ml of conc. hydrochloric acid and 30 ml of 96% ethanol As a result, the number of hexosamine in LPS1, LPS2 or LPS3 was 9±1, 7±1 or 5±1 per m. w. 5,000.

9) KDO content The KDO (2-keto-3-deoxyoctonate) content was determined as follows on the basis of the diphenylamine method (Shaby R. et al., "*Analytical Biochem.*", 58(1), pp. 123-129, 1974).

A KDO detection reagent was prepared by combining 500 mg of dipenylamine, 5 ml of ethanol, 45 ml of glacial acetic acid and 50 ml of conc. hydrochloric acid (all commercially available from Wako-junyaku Co. in Japan). A 500 μl portion of the prepared reagent was combined with 250 μl of distilled water containing any of 0.505 mg/ml of LPS1, 0.576 mg/ml of LPS2 and 0.518 mg/ml of LPS3. The resulting mixture was heated in a boiling water bath at 100° C. for 33 minutes and then cooled in cooling water at 24.5° C. for 30 minutes.

The UV absorption of the mixture was determined at 420, 470, 630 and 650 nm to provide data $A_{420}$, $A_{470}$, $A_{630}$ and $A_{650}$, respectively. As the standard sample, there was used 250 μl of distilled water containing 0.5 μ mole/ml of ammonium salt of KDO (Sigma Co. in U.S.A.). The value S for the test and standard samples was calculated according to the following equation:

$$S = A_{420} - A_{470} + A_{630} - A_{650}$$

The value of the test sample ($S_t$) was 0.109 for LPS1, 0.078 for LPS2 and 0.099 for LPS3, whereas that of the standard sample ($S_s$) was 0.246. The value of distilled water was 0.005. The comparison of these values suggests that LPS1, LPS2 and LPS3 contain $2 \pm 1$, $1 \sim 2$ and $2 \pm 1$ of KOD per m. w. 5,000.

As an example, in the case of LPS1, the KOD content of the solution x (μ mole/ml) may be determined by the equation:

$$\frac{0.5}{0.246} = \frac{x}{0.109}$$

According to the above equation, x is determined to be 0.221. Thus the molar number of KOD contained in 1 mole of LPS1 is determined to be 2.19 according to the following equation on the assumption that 1 mole of LPS1 is m. w. 5,000.

$$y = x \times 10^{-6} \times \frac{5,000}{0.505 \times 10^{-3}} = 2.19$$

Illustrative embodiments of preparations containing LPS according to the present invention will be given in the following examples wherein the LPS content is in terms of *E. coli* LPS calculated according to the limulus test.

EXAMPLE 2 (tablets)

Wheat LPS: 0.04 g
6% HPC lactose: 178 g
Talc stearate: 8 g
Potato starch: 14 g

The above ingredients were mixed and formed into 400 tablets each weighing 0.5 g and containing 0.1 mg of wheat LPS.

EXAMPLE 3 (solution for internal use)

Chlorella LPS: 1 mg
Purified water: 100 ml

EXAMPLE 4 (ointment)

LPS1 : 0.1 g
Purified lanolin: 80 g
Yellow petrolatum: ad 1,000 g

EXAMPLE 5 (injection)

LPS3 : 0.5 mg
Distilled water for injection: ad 1,000 ml

Experiment 1 (quantitative determination of limulus test-positive vegetable LPS The quantitative determination of limulus test-positive LPS contained in various plants was carried out using Toxicolor System commercially available from Sei-Kagaku Kogyo Co. in Japan.

1) Distilled water for injection was poured in a flat- or round-bottomed plate having 96 wells in a proportion of 180 μl per well. Twenty μl of the test sample (when the sample is a solid, it is dissolved in distilled water for injection) was placed in one of the wells of the plate. Pipetting was effected while stirring with a plate mixer to prepare a ten-fold dilution: hereafter, 20 μl portions of the respective diluted samples may be collected successively to prepare ten-fold serial dilutions including 100-fold, 1000-fold and so on.

In addition, the degree of dilution may be changed as desired by adjusting the quantitative rate of the distilled water for injection to the sample.

2) As the internal standard, a 100,000-fold dilution of a solution containing 1.5 μg/ml of *E. coli* was prepared and used to confirm that the dilution process and the chromogenic behaviors of the limulus test were normal.

3) Thirty-five μl of the ten-fold dilution mentioned in the above 1) placed in a well of another plate followed by addition of 35 μl of LS-1 set of Toxicolor System commercially available from Sei-Kagaku Kogyo Co. in Japan. The mixture was allowed to stand at 37° C. for 30 minutes, then 105 μl of 1M aqueous acetic acid was added to the mixture to terminate the reaction. The absorbance of this sample solution was determined at a wave length of 415 nm using Plate Reader MTP-100, an absorbance meter for 96 wells manufactured by Corona Denki Co. in Japan. Distilled water was used as the background, and 42 pg/ml of the ET-1 set of the Toxicolor System of Sei-Kagaku Kogyo Co. in Japan was used to prepare a calibration curve. This calibration curve was used as the basis to determine the quantity of the limulus test-positive vegetable LPS of the respective test samples; the absorbance of distilled water was assumed to be 0.

Here, the experiments were carried out again at other dilutions when the value did not come within a range of 10– 45 pg/ml because the chromogenic strength was confirmed to depend on the content of the limulus test-positive vegetable LPS within said range in the case where the above-mentioned LS-1 set was used.

The quantitative determination of the diluted sample was calculated according to the following equation:

(the value determined on the calibration curve) × (the degree of dilution)

The results of the experiments are shown in Table 6 where solid samples are reported in units of ng/g, and liquid samples, in units of ng/ml.

In the table, the companies and places referred to in the column of samples, are the suppliers and growing districts of the respective samples. Samples without such referring-to were bought at the Nakano-cho branch of the super store Chujitsuya located in Tsukui-gun in Kanagawa, Japan, and their makers could not be identified.

TABLE 6

| Sample (solid) | Content of limulus test-positive LPS (ng) |
|---|---|
| Gymnosperm | |
| Pinus spp. | 125 |
| (Konan Boeki Co. in Japan) | |
| Monocotyledoneae | |
| Hard wheat seeds | 2,250 |
| (Chiba Flour Milling Co. Ltd. in Japan) | |
| Hard wheat seeds (m.w.: 5,000 or more) | 1,000,000 |
| (Chiba Flour Milling Co. Ltd.) | |
| Hard wheat flour | 7,500 |
| (Chiba Flour Milling Co. Ltd.) | |

TABLE 6-continued

| Sample | |
|---|---:|
| Wheat bran (m.w.: 5000 or more) (Chiba Flour Milling Co. Ltd.) | 300 |
| Wheat germ (Chiba Flour Milling Co. Ltd.) | 1,600 |
| Wheat germ (m.w.: 5000 or more) (Chiba Flour Milling Co. Ltd.) | <10,000 |
| Unpolished rice | 1,100 |
| Rice flour (m.w.: 5000 or more) (Hinomoto Koku-fun Co. in Japan) | 31,000,000 |
| Rice brain | 29,000 |
| Rice brain (m.w.: 5000 or more) | 500,000 |
| Corn flour (m.w.: 5000 or more) (Taiyo Shiro Co. in Japan) | <0.3 |
| Corn grits (m.w.: 5000 or more) (Taiyo Shiro Co. in Japan) | 120 |
| Corn (Wako Shokuryo Co. in Japan) | 200 |
| *Gramineae Sasa* (Sekimoto Bussan Co. in Japan) | 15,000 |
| *Iridaceae Iris* (seeds) | 3,300 |
| Garlic (bulb) | 70 |
| Asparagus (bud) | 4,500 |
| *Zingiber mioga* (flower) | 41,000 |
| *Coix Lacryma-jobi* L. var. *Ma-yuen Stapf* (Uchida Wakan-yaku Co. in Japan) | 2,300 |
| *Pinellia ternata* (Thunb) Breitenbach (Matsu-ura Yakugyo Co. in Japan) | 5,500 |
| *Ophiopogon japonicus* Ker-Gawl. var. *genuinus* Maxim., *O. japonicus* Ker-Gawl. (Tochigi Tankaido Co. in Japan) | 4,000 |
| Turmeric (SB Shokuhin Co. in Japan) | 195,000 |
| Dicotyledoneae | |
| Soybean (Sanjo Shokuhin Co. in Japan) | 150 |
| Soybean (m.w.: 5,000 or more) (Hokuren Co. in Japan) | 400 |
| "Adzuki" bean (Wako Shokuryo Co. in Japan) | 450 |
| "Adzuki" bean (m.w.: 5,000 or more) (Wako Shokuryo Co.) | 36,000,000 |
| Broad bean (raw) | 750 |
| Potato (m.w.: 5,000 or more) (Hokuren Co.) | <0.3 |
| Japanese medlar (seed) | 800 |
| Avocado (seed) | 950 |
| Peach (seed) | 4,500 |
| Walnut (seed) | 1,900 |
| Broad bean (seed) | 750 |
| Pumpkin (seed) | 10,000 |
| Tomato (raw berry) | 10,500 |
| "*Kaiware daikon*" (Japanese radish) (except root) | 50,000 |
| *Actinidia polygama Maxim.* (Marukyu Bussan Co. in Japan) | 40,000 |
| *Gynostemma pentaphyllum* (Thunb.) Makino (K.K. Sakurai in Japan) | 73,000 |
| *Houttuynia cardata* Thunb (on wet weight basis) (Medicinal plant garden belonging to Teikyo University in Japan) | 1,200 |
| White pepper (SB Shokuhin Co.) | 2,300 |
| *Capsicum annuum* L. (Konan Boeki Co. in Japan) | 2,300 |
| *Illicium verum* Hook. fil. (Konan Boeki Co.) | 5,500 |
| Nutmeg (Lion Co. in Japan) | 2,000 |
| Sour orange (Uchida Wakanyaku Co.) | 8,000 |
| Kudzu-vine (Tochigi Tenaido Co.) | 3,000 |
| *Glycyrrhiza glabra* L. var. *glandulifera Regal et Herder* (Uchida Wakanyaku Co.) | 18,000 |
| Carrot (Uchida Wakanyaku Co.) | 45,000 |
| *Seseli libanotis* Koch var. *daucifolia DC.* (Tochigi Tenkaido Co.) | 50,000 |
| *Sinomenium acutum* Rehd. et Wils (Tochigi Tenkaido Co.) | 600,000 |
| *Uncaria rhynchophylla Miq., Ourouparia rhynchophylla Matsum.* (Uchida Wakanyaku Co.) | 7,000 |
| Hachimi-jiwogan (Kanebo Yakuhin in Japan) | 17,000 |
| Shosaikoto (Tsumura in Japan) | 13,000 |
| Goreito (Tsumura in Japan) | 12,000 |
| Choreito (Tsumura in Japan) | 14,000 |
| Juzendaihoto (Tsumura in Japan) | 8,000 |
| Hachimi-jiwogan (Tsumura in Japan) | 8,000 |
| Royal jelly (Pekin Royal Jelly) | 1,000 |
| Honey (Kato Bihoen Honpo Co. in Japan) | 800 |
| Pteridophyta | |
| Horse tail (on wet weight basis) (Medicinal plant garden belonging to Teikyo University in Japan) | 700 |
| Royal fern (Sekimoto Bussan Co. in Japan) | 10,000 |
| Algae | |
| *Undaria pinnatifida Suringar* (Sanriku district in Japan) | 11,000 |
| Bud of *Undaria pinnatifida Suringar* (Moriya Kenko Shokuhin Co. in Japan) | 200,000 |
| *Hijikia fusiformis* (raw) | 85,000 |
| Bud of *Hijikia fusiformis* (Sho-zen Hon-ten in Japan) | 105,000 |
| Kelb (Yamato Takahasi Co. in Japan) | 235,000 |
| *Asakusa laver* (dried raw laver) | 130,000 |
| Chlorella | |
| (Healstar Japan YS Co. in Japan) | 1,900,000 |
| (Mannan foods YS Co. in Japan) | 1,000,000 |
| Fungi | |
| *Lentinus edodes* Sing., *Cortinellus shiitake* P. Henn. (Shimonita in Shizuoka, Japan) | 16,000 |
| Winter mushroom (Nakano City in Nagano, Japan) | 20,000 |
| *Lyophyllum shimeji* (Sega-gun, Miyagi-machi in Gunma, Japan) | 40,000 |
| *Polyporales Grifola* (Ohtone in Japan) | 205,000 |
| Awabitake (Hanyu in Japan) | 8,000 |
| Mushroom | 20,000 |
| Jew's ear | 75,000 |
| *Pholiota nameko* | 21,000 |
| Ebios (Brewer's yeast manufactured by Asahi Beer Co. in Japan) | 250,000 |
| *Cordyceps sinensis Sacc., Cordyceps sobolifera* | 240,000 |

| Sample (Liquid) | Limulus test-positive LPS (ng) |
|---|---:|
| Beer | |
| Kirin's FINE PILSNER | 1,150 |
| LAGER BEER | 1,250 |
| HEARTLAND | 1,550 |
| FINE DRAFT | 1,400 |
| Asahi's SUPER YEAST | 600 |
| Wine | |
| Suntory's Ste. Neige (white) | 13 |
| (red) | 24 |
| Cidre (apple) | 900 |
| Sake (Japanese liquor) | |
| Ozeki, first grade (Ozeki Shuzo Co.) | 2.4 |
| Kizakura, second grade (Kizakura Shuzo Co.) | 1.7 |
| Taikan Ginjo, second grade (Gyokusendo Shuzo Co.) | 2.1 |
| Sake from unpolished rice Hibi Ikkon (Ozeki Shuzo Co.) | 12 |
| Herb liquor Totoshu DELCUP (Totoshu Honpo Co. in Japan) | 1.2 |
| Shochu (Japanese low-class distilled spirits) TAKARA SHOCHU (Takara Shuzo Co. in Japan) | <2.0 |
| Others | |
| KYOLEOPIN (Wakunaga Seiyaku Co. in Japan) | 600 |
| Garlic extracts (Wakunaga Seiyaku Co. in Japan) | 350 |
| Gross Q (Chlorella Kogyo Co. in Japan) | 6,000 |
| Ohmugi Kenko Mekkoru (Ichiwa in Korea) | 2,000 |
| Sacron Herb Solution (Ezai in Japan) | 1,000 |
| Extracts of dishcloth gourd | 700 |
| Bio-arugen (Chlorella Kogyo Co. in Japan) | 400 |
| Pan-siron Naifukueki (Rhoto Seiyaku Co. in Japan) | 200 |
| Yunkeru Fantie (Sato Seiyaku Co. in Japan) | 50 |
| Korihogusu (Kobayashi Seiyaku Co. in Japan) | 30 |
| Today (Sankyo in Japan) | 20 |
| Mio D Kowa 100 (Kowa in Japan) | 10 |
| Ri-gein (Sankyo in Japan) | 9 |
| Roburen 50 (Dai-ichi Seiyaku in Japan) | 7 |
| Sorumack (Taiho Seiyaku in Japan) | 6 |
| Ro-jerry Gold (Chugai Seiyaku in Japan) | 5 |
| Pas-bitan 30 (Tokiwa Seiyaku in Japan) | 5 |

TABLE 6-continued

| | |
|---|---|
| Thio-bita (Taiho Seiyaku in Japan) | 5 or less |
| Ripobitan (Taisho Seiyaku in Japan) | 5 or less |
| Aspara Gold (Tanabe Seiyaku in Japan) | 5 or less |

Experiment 2 (choice of LPS whose macrophage activation $ED_{50}$ is 0.4–100 ng/ml of culture solution in terms of its limulus test-positive LPS content)

Two hundred μl ($2 \times 10^5$ cells)/well of macrophage peritoneal cells of mice (each group comprised three mice of 9 weeks old and having an average weight of 29 g) were placed in a flat-bottomed plate having 96 wells, and 10 μl of recombinant IFN-γ (100 units/ml) as a primer was placed in the respective wells. Separately, extracts prepared by extraction of various LPS sources with hot water at 65° C. for 5 hrs. were diluted to various degrees, and then were administered as triggers to the cells three hours after the administration of the primer in a proportion of 10 μl/well. After two hour culture, the culture solutions were subjected to centrifugation at 3,000 G for 20 min. A pipette was used to collect 130 μl of the supernatant from the respective wells, and the TNF activity was determined on the basis of the toxicity to L929 cells. The limulus test-positive LPS content was determined using Toxicolor System ® commercially available from Sei-Kagaku Kogyo Co. in Japan.

The values were plotted to prepare a graph wherein the quantity of the TNF produced (units/ml of culture solution) was plotted along the axis of ordinate, whereas the corresponding limulus test-positive LPS content (ng/ml of culture solution) was plotted along the axis of abscissa (on a logarithmic scale), and a sigmoid curve was prepared on the basis of the plotted points. The macrophage activation ability was estimated to be 0% in the case where it corresponded to the quantity of TNF produced by macrophage with no trigger added thereto, and 100% was assigned to the macrophage activation ability which provided the maximal constant of TNF. The limulus test-positive LPS content supposed to provide 50% of macrophage activation ability was determined with reference to the curve.

Table 7 given below shows the data of the LPS sources satisfying the above-mentioned correlation between the macrophage activation ability and the limulus test-positive LPS content. In the table, "TNF", "activation ability" and "LPS" represents the quantity of the TNF produced (units/ml of culture solution), macrophage activation ability (%) and limulus test-positive LPS content (ng/ml of culture solution), respectively. Here, the quantity of the TNF produced in the case where no trigger was added was 0.75 units/ml, so the macrophage activation ability was determined to be 0% in the case where the quantity of the TNF produced was 0.75 units/ml or less. The macrophage activation ability (%) was calculated according to the following equation:

$$\frac{\text{Quantity of TNF produced} - 0.75}{\text{Maximal constant of TNF} - 0.75} \times 100$$

TABLE 7

| LPS sources | TNF | Activation ability | LPS |
|---|---|---|---|
| Turmeric | 0.75 | 0 | 0 |
| | 3.9 | 9 | 0.6 |
| | 36.3 | 100 | 60 |
| | 36.3 | 100 | >1000 |
| Sinomenium acutum Rehd. et Wils. | 0.75 | 0 | 0 |
| | 40.7 | 100 | 4 |
| | 36.5 | 90 | 400 |
| | 40.7 | 100 | >1000 |
| Kelp (Laminaria japonica) | 0.75 | 0 | 0 |
| | 1.3 | 4 | 0.8 |
| | 13.0 | 100 | 80 |
| | 13.0 | 100 | >1000 |
| Asakusa laver (Porphyra tenera) | 0.75 | 0 | 0 |
| | 1.0 | 2 | 0.3 |
| | 12.8 | 100 | 30 |
| | 12.8 | 100 | >1000 |
| Extracts of Undaria pinnatifida Suringar (bud) | 0.75 | 0 | 0 |
| | 1.3 | 4 | 0.2 |
| | 15.5 | 100 | 20 |
| | 15.5 | 100 | >1000 |
| Hijikia furiformis (bud) | 0.75 | 0 | 0 |
| | 5.7 | 8 | 0.7 |
| | 62.7 | 100 | 70 |
| | 62.7 | 100 | >1000 |
| Ebios | 0.75 | 0 | 0 |
| | 0.6 | 0 | 0.7 |
| | 30.6 | 100 | 70 |
| | 30.6 | 100 | >1000 |
| Cordyceps sinensis Sacc., Cordyceps sobolifera | 0.75 | 0 | 0 |
| | 2.0 | 4 | 0.4 |
| | 30.3 | 100 | 40 |
| | 30.3 | 100 | >1000 |
| Undaria pinnatifida Suringar (bud) | 0.75 | 0 | 0 |
| | 0.9 | 1 | 0.4 |
| | 22.7 | 100 | 40 |
| | 22.7 | 100 | >1000 |
| Chlorella | 0.75 | 0 | 0 |
| | 39.2 | 100 | 9.6 |
| | 35.0 | 89 | 960 |
| E. coli LPS | 0.75 | 0 | 0 |
| | 3.6 | 27 | 2 |
| | 10.2 | 89 | 20 |
| | 11.4 | 100 | 200 |
| | 10.9 | 95 | 2000 |
| Wheat LPS | 0.75 | 0 | 0 |
| | 0.7 | 0 | 2 |
| | 10.1 | 99 | 21 |
| | 10.2 | 100 | 210 |
| | 8.5 | 82 | 2100 |
| B. pertussis | 0.75 | 0 | 0 |
| | 0.7 | 0 | 11 |
| | 3.3 | 55 | 110 |
| | 5.4 | 100 | 1100 |
| Lipid A | 0.75 | 0 | 0 |
| | 4.7 | 37 | 2 |
| | 9.4 | 80 | 24 |
| | 11.1 | 96 | 240 |
| | 11.5 | 100 | 2400 |

The results given in Table 3 are shown in FIGS. 5–8.

In FIGS. 5–8, the axis of ordinate represents the macrophage activation activity (%), whereas the axis of abscissa (on a logarithmic scale) represents the limulus test-positive LPS content (ng/ml of culture solution).

Figure 5:
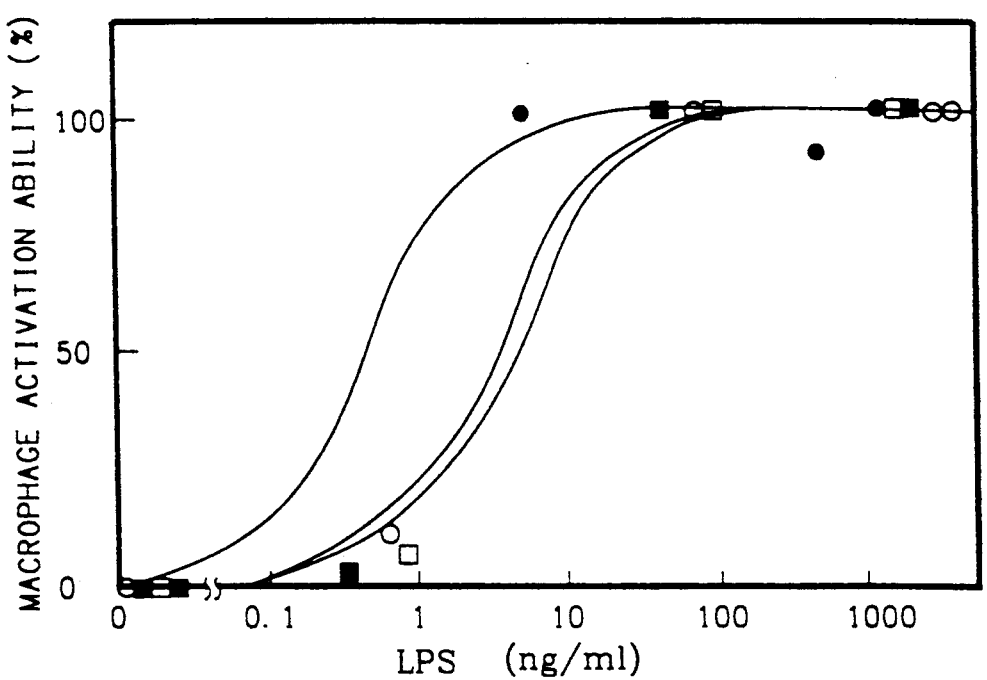
FIGS. 5 to 8 are graphs evidencing the correlation between the macrophage activation ability and the limulus test-positive LPS content within the purview of the present invention.

In FIG. 5, ○, ●, □, and ■ show the data of Turmeric, Sinomenium acutum Rehd. et Wils., Kelp and Asakusa laver, respectively.

Figure 6:
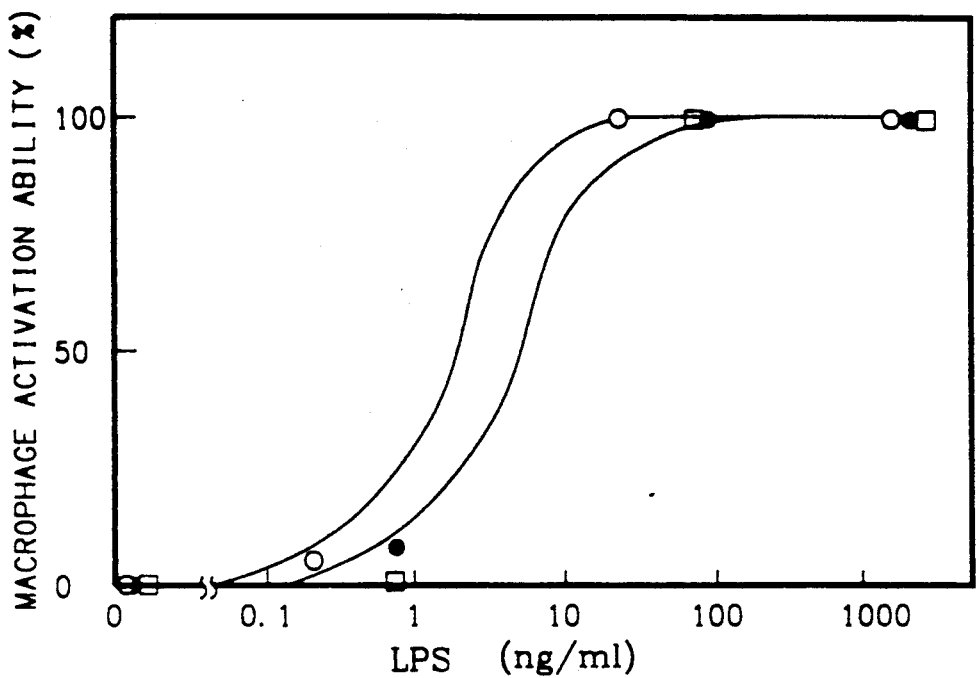

In FIG. 6, ○, ● and □ show the data of extracts of Undaria pinnatifida Suringar (bud), Hijikia fusiformis (bud) and Ebios, respectively.

Figure 7:
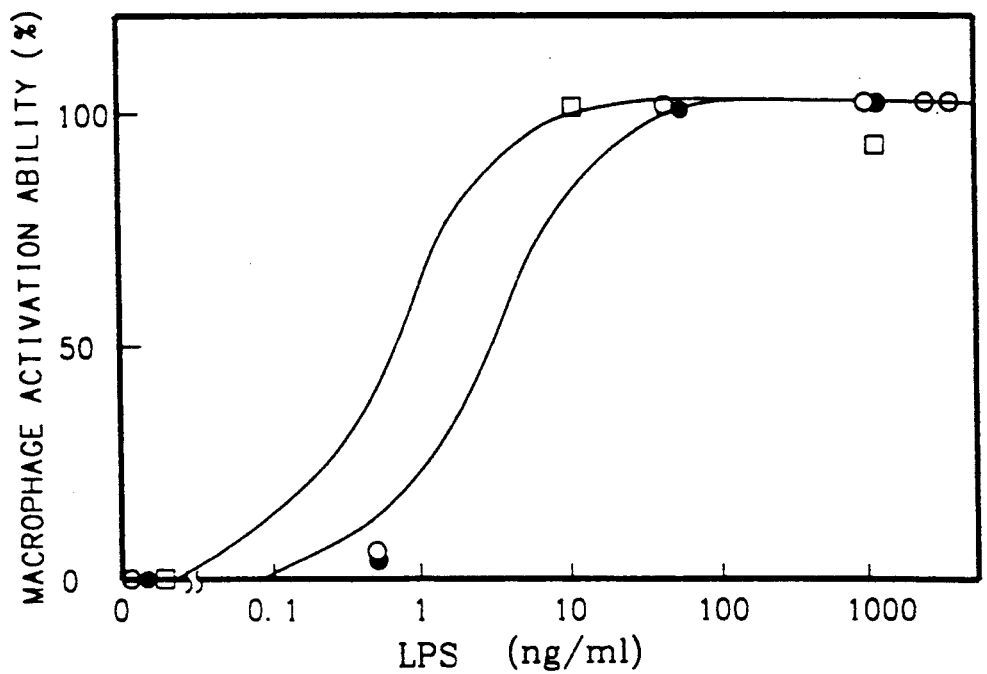

In FIG. 7, ○, ● and □ show the data of Cordyceps sinensis Sacc., Cordyceps, sobolifera, Undaria pinnatifida Suringar (bud) and Chlorella, respectively.

Figure 8:
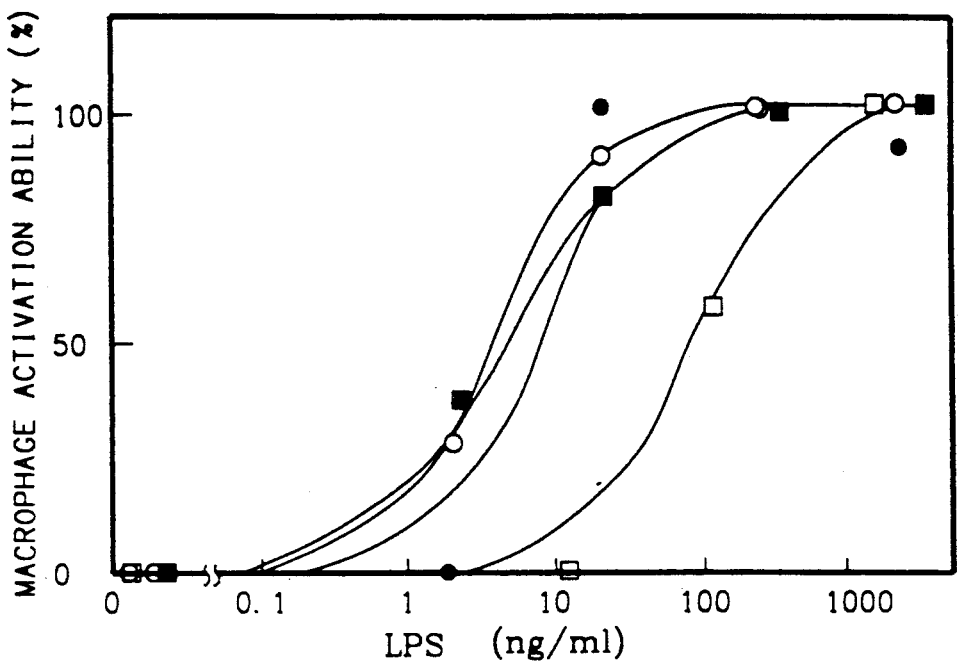

In FIG. 8, ○, ●, □, and ■ show the data of E. coli LPS, wheat LPS, B. pertussis LPS and lipid A, respectively.

Experiment 2 (Analgesic effects on experimetal animals-1)

1) To six-membered groups of 8 week old C3H/He male mice whose body weight being 20-25 g, there was intravenously administrated 0.2 ml of distilled water containing 0, $10^{-4}$, $10^{-3}$, $10^{-2}$, $10^{-1}$, 1 and 10 μg/moused of LPS of the present invention (wheat LPS prepared in Reference Example 1). Three hours later, 0.5 ml of 1% acetic acid was given to the mice intraperitoneally. The frequency of writhing of the respective mice was counted for 30 minutes. The results are shown in Table 8 as an average of 6 mice in the respective groups. In the table, the writhing inhibition (%) was calculated by the following equation.

{1 − [(frequency of writhing at the dose)−(that at 400 μg)]/[(frequency of writhing at 0 μg)−(that at 400 μg)]} × 100

TABLE 8

| Dose (μg/mouse) | Writhing frequency | Writhing inhibition (%) |
|---|---|---|
| 0 | 33 | 0 |
| $10^{-4}$ | 27 | 18 |
| $10^{-3}$ | 23 | 30 |
| $10^{-2}$ | 16 | 52 |
| $10^{-1}$ | 17 | 48 |
| 1 | 4 | 88 |
| 10 | 4 | 88 |

According to the double-sided t test, significant analgesic effects were judged to be produced at a dose of $10^{-2}$ μg/mouse or more at a risk less than 1%, and at a dose of 1 μg/mouse or more at a risk less than 0.1%.

Figure 9:
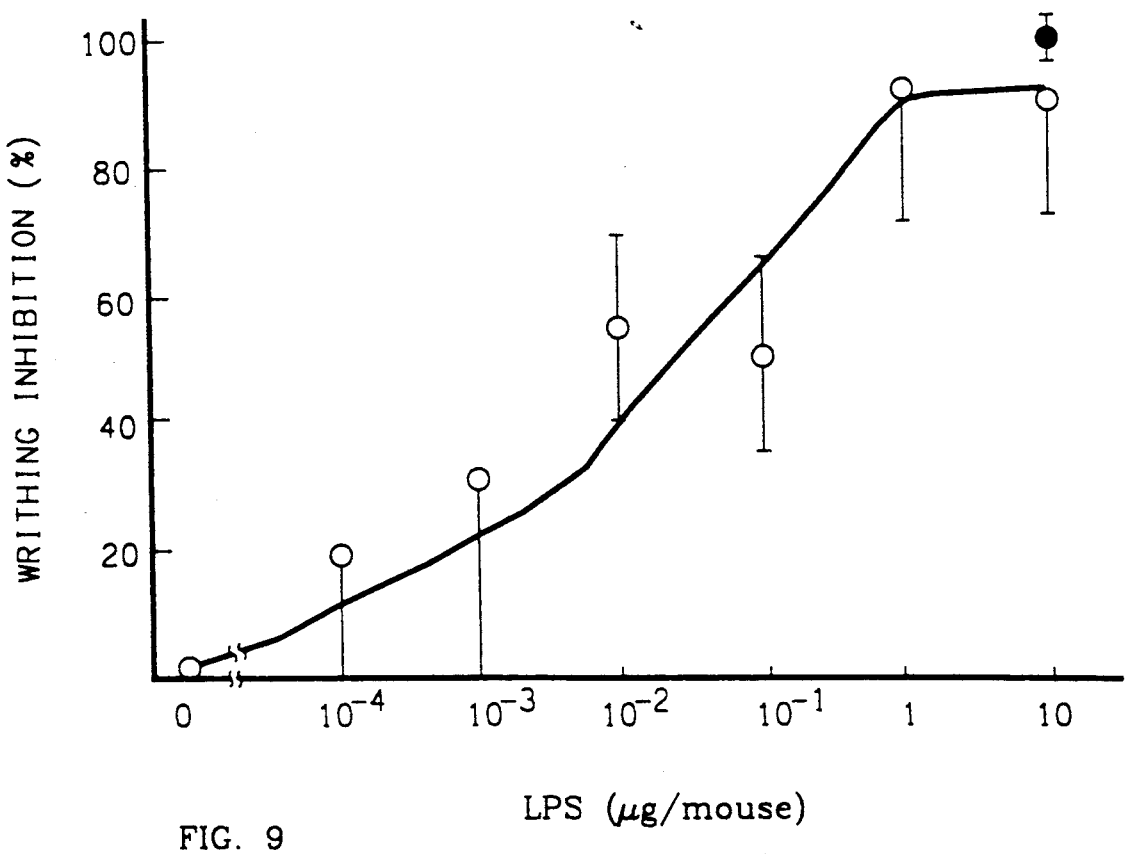
FIG. 9 is a graph showing the dose-response curve of the analgesic effects of the LPSs of the present invention

FIG. 9 is a graph showing the writhing inhibition given in Table 7 (indicated with ○ in the figure), and that of E. coli LPS (0128:B8 of Difco in U.S.A.) (indicated with ● in the figure). The data of E. coli LPS shows the writhing inhibition 96% calculated on the basis of the average writhing frequency at the dose of 10 μg/mouse and the corresponding value 24 in the control group.

As is apparent from the figure, about 90% of writhing caused by acetic acid was inhibited at a weight dose of 1 μg/mouse of the LPS of the present invention.

2) The following preparations were given to six-membered groups of 8 week old C3H/H male mice (body weight: 20-25 g).

Group A: an intravenous solution prepared by dissolving 1 μg by weight/mouse of LPS (wheat LPS prepared in Reference Example 1) in 0.2 ml of physiological saline.

Group B: an intravenous solution prepared by dissolving 1 mg/mouse of the prior art analgesic phenylbutazone in 0.2 ml of 1% aqueous CMC solution.

Group C: 0.2 ml of physiological saline.

0.5 ml of 1% acetic acid was administered intraperitoneally 0.5, 1.5, 3, 8 or 18 hours after the administration of the preparations, and the writhing frequency of the respective mice was counted. The results are shown in Table 9 as an average of six mice in the respective groups. In the table, the writhing inhibition (%) was calculated as follows:

$$\left(1 - \frac{\text{Writhing frequency in the respective groups}}{\text{Writhing frequency in the group } C}\right) \times 100$$

In the above equation, the writhing frequency in the group C is that obtained in the case where acetic acid was given 30 minutes after the administration of physiological saline, and the counting was made for 30 minutes. The data of the group A was 39, whereas that of the group B was 35.

TABLE 9

| | Writhing frequency (writhing inhibition %) | |
|---|---|---|
| Time lapsed | Group A | Group B |
| 0.5 | 20 (49) | 18 (49) |
| 1.5 | 7 (82) | 7 (80) |
| 3 | 9 (77) | 25 (29) |
| 8 | 26 (33) | Not determined |
| 18 | 25 (36) | Not determined |

Figure 10:
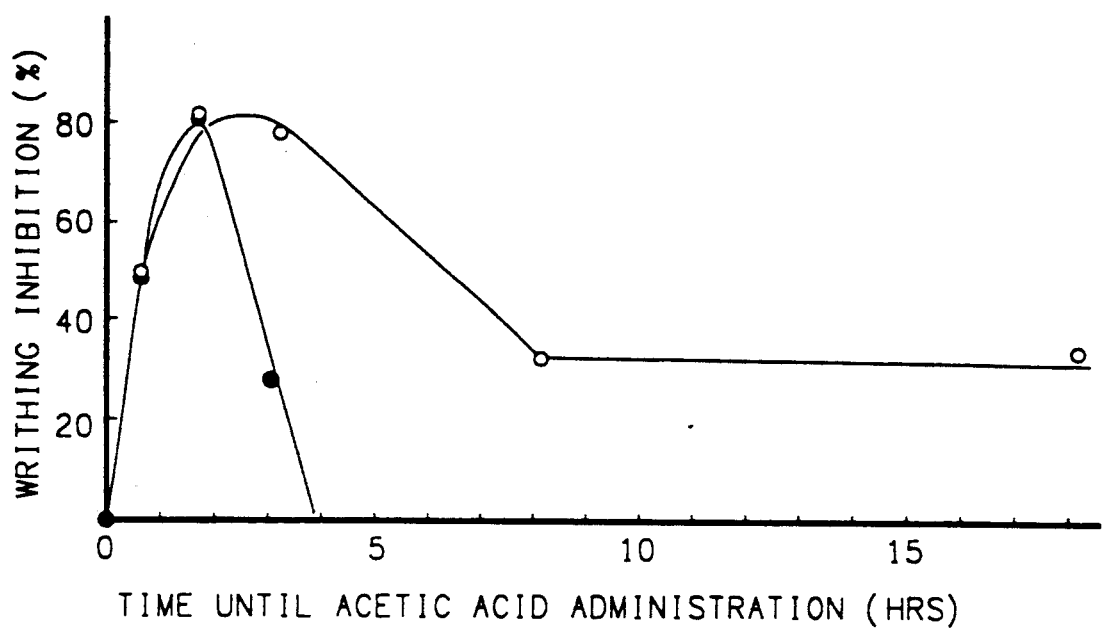
FIG. 10 is a graph showing the analgesic effects of the LPSs of the present invention in comparison with those of the prior art analgesic phenylbutazone.

FIG. 10 is a graph showing the writhing inhibition given in Table 9. In the figure, ○ and ● are data of Groups A and B, respectively.

As is apparently shown in Table 9 and FIG. 10, the LPS of the present invention showed analgesic effects of the same as or better than phenylbutazone at a surprisingly small dose; a thousandth of phenylbutazone, and the effects were produced almost at the same time as phenylbutazone. In addition, according the the double-sided t test, significant analgesic effects of the LPS of the present invention were observed even 8 to 18 hours after the administration at a risk of 5% or less, whereas phenylbutazone was judged to have no significant analgesic effects 3 hours after the administration. Namely, the analgesic affects of the LPS of the present invention may be said to last for a very long time as compared with phenylbutazone.

Experiment 4 (Analgesic effects on experimental animals - 2)

To five-membered groups of 7 to 10 week old C3H/He male mice having an average body weight of 28 g, there was orally administrated 200 μl of distilled water containing 0, 1, 5, 25 or 400 μg/mouse of LPS3 or E. coli LPS using a probe. One and a half hours later, 500 μl of 0.7% acetic acid was given to the mice intraperitoneally over a period of 5 minutes. The frequency of writhing of the respective mice was counted, and the results as shown in Table 10 were recorded (an average of 5 mice in the respective groups). In the table, "−" reflects that the determination was not made at said dose. The writhing inhibition (%) was calculated by the following equation.

{1 − [(frequency of writhing at the dose)−(that at 400 μg)]/[(frequency of writhing at 0 μg)−(that at 400 μg)]} × 100

TABLE 10

| | LPS3 of the present invention | | E. coli LPS | |
|---|---|---|---|---|
| LPS dose (μg/mouse) | Writhing frequency | Writhing inhibition (%) | Writhing frequency | Writhing inhibition (%) |
| 0 | 18 | 0 | 20 | 0 |
| 1 | 17 | 10 | 18 | 82 |
| 5 | 10 | 80 | — | — |

TABLE 10-continued

| LPS dose (μg/mouse) | LPS3 of the present invention | | E. coli LPS | |
|---|---|---|---|---|
| | Writhing frequency | Writhing inhibition (%) | Writhing frequency | Writhing inhibition (%) |
| 25 | 7 | 110 | 13 | 64 |
| 400 | 8 | 100 | 9 | 100 |

Experiment 5 ((Analgesic effects on experimental animals - 3)

To the six-membered groups of 7 week old C3H/He male mice (average body weight: about 23 g), there was administered intravenously 200 μl of physiological saline prepared so that it contains 1 μg/mice of A. radiobacter LPS, LPS3 or E. coli LPS in terms of limulus activity. The control group received only physiological saline. 1.5 hours after that, 500 μl of 1% acetic acid was administered intraperitoneally over a period of 5 minutes, and the writhing frequency of the respective mice was counted. As a result, as an average of 6 mice in the respective groups, 17 frequencies of writhing was observed in the control group, whereas only 8 frequencies of writhing, which are less than half of the value of the control group, was observed in LPS-received groups.

Experiment 6 ((Analgesic effects on experimental animals-3)

To the five-membered groups of 8 week old C3H/He male mice (average body weight: about 29 g), there was administered orally 200 μl of physiological saline prepared so that it contains 0, 0.7, 3.5 or 17.5 μg/mice of powder A-a2 prepared in Reference Example 1 using a probe. 1.5 hours after that, 500 μl of 0.7% acetic acid was administered intraperitoneally over a period of 5 minutes, and the writhing frequency of the respective mice was counted for 30 minutes. As a result, as an average of 5 mice in the respective groups, the data shown in Table 11 was recorded. In the table, "—" means that the determination was not made at the dose, and the writhing inhibition (%) was calculated according to the following equation:

$$\{1 - [(\text{frequency of writhing at the dose}) - (\text{that at } 17.5\ \mu g)]/[(\text{frequency of writhing at } 0\ \mu g) - (\text{that at } 17.5\ \mu g)]\} \times 100$$

TABLE 11

| LPS dose (μg/mouse) | Powder A-a2 | |
|---|---|---|
| | Writhing frequency | Writhing inhibition (%) |
| 0 | 18 | 0 |
| 0.7 | 11 | 64 |
| 3.5 | 7 | 100 |
| 17.5 | 7 | 100 |

Figure 11:
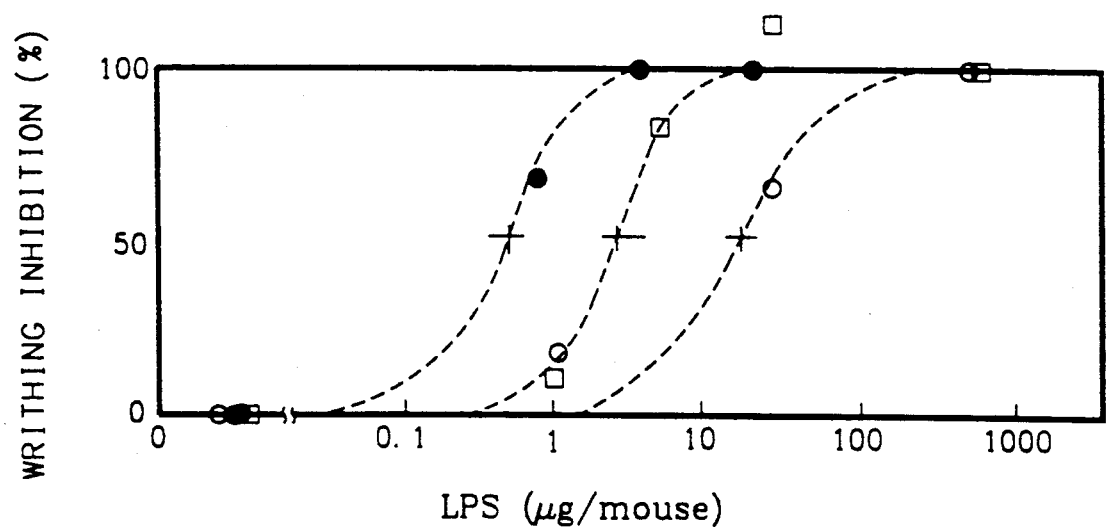
FIG. 11 is a graph showing the analgesic effects of the LPSs of the present invention.

FIG. 11 is a graph reflecting the results shown in Tables 10 and 11. FIG. 2 shows that the writhing inhibition $ED_{50}$ of LPS3, Powder A-a2, and E. coli LPS is estimated to be 2.8, 0.46 or 17 μg/mouse. Thus it is supposed that the analgesic effect of LPS3 is about six times as of E. coli LPS, and the powder A-a2 is about 36 times effective as compared with E. coli LPS.

Experiment 7 (Clinical analgesic effects)

Patient A (female, 41 years old)

1986: Infected with HIV through heterosexual intercourse
August in 1990: ARC
p24 antibody:+
Aug. 20, 1990: Started to administer 400 mg/day of AZT.
Sep. 28, 1990: Two left femoral eruptions were found.
Oct. 4, 1990: VZV attained left hip, left femoral and left calf portions.
Oct. 5, 1990: Hospitalized.
Leukocyte number: 4,000
C reactive protein: 0.25
T4 cells: 196
Pain:+++

Forty ml of a 50 w/v % glycerin solution (glycerin:water=1:1) containing 1 mg/ml of powder A-a2 prepared in Reference Example 1 (1 μg/ml in terms of limulus test-positive LPS) was applied directly to VZV area once a day, and 1 ml of the glycerin solution was orally administered three times a day. No other drug was used. As a result, the pain was drastically eliminated in some hours after the application, and most of the eruptions disappeared in about one week.

Dose, interval and toxicity

The dose and the interval of the analgesics and veterinary analgesics of the present invention are of course determined by the doctor or veterinarian in charge individually in view of the age, conditions, etc. of the patient. However, it may be said that 1 μg–100 mg (oral administration), 10 ng–10 mg (intravenous administration) and 100 ng–1 mg (percutanous administration) are standard single dose per day to adults (body weight 60 kg). For veterinary use, about one sixtieth of the above quantities may be given per 1 kg of body weight of large-sized animals such as cattle, horses or the like. About twice as much as the dose to large-sized animals may be given per 1 kg of body weight of medium- or small-sized animals such as pigs, dogs, cats or the like. Fowls or the like may receive twice as much as the dose to medium- or small-sized animals.

The $LD_{50}$ of LPS1, LPS2 and LPS3 in 7 week old C3H/He male mice having an average body weight of 22 g were 150, 180 and 180 μg/mouse according to the Behrens Karber; these values are less than 60% of 300 μg/mouse found for E. coli LPS (0128:B8 manufactured by Difco Co. in U.S.A.). Further, wheat LPS (Reference Example 1), E. coli LPS and B. pertussis LPS had the following $LD_{50}$ (an average of the data on two male BALB/C mice weighing 45 kg on average).

| LPS | $LD_{50}$/kg (mg) | |
|---|---|---|
| | i.v. | i.c. |
| Wheat LPS | 3.2 | 16 |
| E. coli LPS | 3.4 | 16 |
| B. pertussis LPS | 11 | 32 |

What we claim is:

1. A method for the alleviation or prevention of pain in an animal, including human in need of such treatment or prevention, which comprises administering to said animal an effective analgesic amount of a lipopolysaccharide, the lipopolysaccharide having an $ED_{50}$ of 0.4–100 ng/ml of a culture solution thereof in terms of its limulus test-positive lipopolysaccharide content observed on a sigmoid curve which is prepared by determining the ability of the lipopolysaccharide to activate the TNF productivity of macrophage cultured in vitro, and by plotting the macrophage activation ability (%) along the axis of ordinate wherein the ability is estimated to be 0% in the case where it corresponds to the quantity of TNF produced by macrophage with no lipopolysaccharide added thereto, and 100% is assigned to the macrophage activation ability which provides the maximal and constant quantity of TNF produced by the macrophage and plotting the limulus test-positive lipopolysaccharide content of the lipopolysaccharide along the axis of abscissa on a logarithmic scale.

2. The method according to claim 1, wherein the lipopolysaccharide is selected from the group consisting of vegetable lipopolysaccharide, bacterial lipopolysaccharide and lipid A.

* * * * *

UNITED STATES PATENT AND TRADEMARK OFFICE
CERTIFICATE OF CORRECTION

PATENT NO. : 5,281,583
DATED : January 25, 1994
INVENTOR(S) : Gen-Ichiro Soma, et al.

It is certified that error appears in the above-identified patent and that said Letters Patent is hereby corrected as shown below:

Column 18, line 65; change "NIssui" to --Nissui--
Column 21, line 62; change "unde" to --under--
Column 23, lines 53 and 58; change "didrogen" to --hydrogen--
Column 27, line 25; change "Tankaido" to --Tenkaido--
Column 27, line 53; change "Tenaido" to --Tenkaido--
Column 28, line 21; change "Sega-gun" to --Seta-gun--
Column 30, lines 19-20; change "furiformis" to --fusiformis--
Column 31, line 8; change "moused" to --mouse--
Column 32, line 31, change "the the" to --the--

Signed and Sealed this

Twenty-sixth Day of July, 1994

Attest:

BRUCE LEHMAN

Attesting Officer

Commissioner of Patents and Trademarks